US011351253B2

(12) United States Patent
Papavassilis et al.

(10) Patent No.: US 11,351,253 B2
(45) Date of Patent: *Jun. 7, 2022

(54) METHODS OF TREATING PALMOPLANTAR PUSTULAR PSORIASIS (PPP) USING IL-17 ANTIBODY

(71) Applicant: NOVARTIS AG, Basel (CH)

(72) Inventors: Charis Papavassilis, Lorrach (DE); Oliver Sander, Basel (CH); Tomohiro Shima, Tokyo (JP); Susumu Kitamura, Yokohama (JP)

(73) Assignee: NOVARTIS AG, Basel (CH)

( * ) Notice: Subject to any disclaimer, the term of this patent is extended or adjusted under 35 U.S.C. 154(b) by 74 days.

This patent is subject to a terminal disclaimer.

(21) Appl. No.: 16/555,391

(22) Filed: Aug. 29, 2019

(65) Prior Publication Data

US 2020/0085945 A1    Mar. 19, 2020

Related U.S. Application Data

(63) Continuation of application No. 14/911,387, filed as application No. PCT/IB2014/063902 on Aug. 13, 2014, now Pat. No. 10,434,172.

(60) Provisional application No. 61/866,242, filed on Aug. 15, 2013.

(51) Int. Cl.
| | | |
|---|---|---|
| *A61K 39/395* | (2006.01) | |
| *C07K 16/24* | (2006.01) | |
| *A61K 45/06* | (2006.01) | |
| *A61K 39/00* | (2006.01) | |

(52) U.S. Cl.
CPC .......... *A61K 39/3955* (2013.01); *A61K 45/06* (2013.01); *C07K 16/244* (2013.01); *A61K 2039/505* (2013.01); *A61K 2039/545* (2013.01); *C07K 2317/21* (2013.01); *C07K 2317/34* (2013.01); *C07K 2317/76* (2013.01); *C07K 2317/92* (2013.01); *C07K 2317/94* (2013.01)

(58) Field of Classification Search
CPC ... C07K 16/244; C07K 2317/76; A61P 17/06; A61K 2039/505; A61K 2039/545
See application file for complete search history.

(56) References Cited

U.S. PATENT DOCUMENTS 6,309,636 B1  10/2001  do Couto ........... A61K 51/1051
                                                424/133.1

FOREIGN PATENT DOCUMENTS

| WO | WO-2006013107 A1 * | 2/2006 | ............. A61P 17/06 |
| WO | WO2012/045848 A1 | 4/2012 | |

OTHER PUBLICATIONS

Murakami et al. Patients with palmoplantar pustulosis have increased IL-17 and IL-22 levels both in the lesion and serum. Exp. Dermatol., Oct. 2011; 20(10): 845-7.*
Declaration of Dr. Charis Papavassilis, dated Aug. 21, 2018 (including Exhibits A-Y).
Declaration of Inventor Tomohiro Shima, dated Sep. 18, 2018 (including Exhibits A-G).
Croxtall (2011) Drugs 71(3):1733-1753.
Wenk et al (2011) J Am. Acad. Derm. 64(2), Suppl. 1, AB151.
Varman et al. (2014) Burns 40:e35-e39.
Letko et al. (2013) Invest Opthalmol Vis. Sci 54:E-Abstract 5929.
Novartis Clinical Trial Results Database, CAIN457A1302, available at https://www.novctrd.com/CtrdWeb/displaypdf.nov?trialresultid=16007, dated Dec. 16, 2016.
Stanbury and Graham (1998) Br J Ophthalmol 82:704-708.
Ali et al. (2013) Drug Health Care Patient Saf. 5:79-99.
Honma et al. (2017), Abstract, Presented at 32nd Ann. Meeting Japanese Soc. Psoriasis Res., Sep. 8-9, 2017, Tokyo, Japan (English translation).
KOINN-KA (Japanese Journal of Oral and Maxillofacial Surgery), (2000, vol. 12(2), pp. 153-159 (English Translation).
Capon (2013) J. Invest Dermatol 13:2503-2504.
Stanbury and Graham (1998) Br J Ophthamol 82:704-708.
Polesie and Lidholm (2016) Acta Derm Venoreol. 97:124-125.
Hueber et al. (2012) Gut 61:1693-1700.
Heller and Shiffman (1985) Can Med Assoc J. 132:1129-36.
Suguira et al. (2013) J. Invest. Derm., 133, 2514-2521.
Menter et al. (2009) J Am Acad Dermatol 81:451-86.
Written Opinion of the International Searching Authority for PCT/IB2014/063902 dated Dec. 3, 2014.
Korber et al. (2013) J. Invest. Derm., 133:2634-2637.
Mugheddu et al. (2017) JEADV 31, e386-e427.
Onoutriadis et al. (2011) Am J Hum Genet. 89(3): 432-437.
Iwatsuki Ket al. (2010) Jpn J Dermatol 2010, 120:815-39.
Imafuki et al. (2016) J. Dermatol 43:1101-1107.
Ebert et al (2008) Clin Exp Immunol. 154(3): 325-331.
Dauden et al. (2010) Br J Dermatol. 183(6):1346-7.
Burmester et al. (2009) Ann Rheum Dis. 68:1863-1869.
AnaptysBio Press Release, Apr. 16, 2015, AnaptysBioat.

(Continued)

*Primary Examiner* — Dong Jiang
(74) *Attorney, Agent, or Firm* — David Goetz

(57) ABSTRACT

The disclosure is directed to methods, treatment regimens, uses, kits and therapies for treating Generalized Pustular Psoriasis (GPP). These methods, treatment regimens, uses, kits and therapies utilize, inter cilia, administration of an IL-17 antagonist, e.g., an IL-17 antibody, such as secukinumab. Additionally disclosed are improved methods for treating plaque-type psoriasis that utilize up-titration and down-titration of the IL-17 antagonist, e.g., an IL-17 antibody, such as secukinumab, as well as modification of dose frequency. Further disclosed are methods of treating palmoplantar pustular psoriasis using the disclosed IL-17 antagonists, e.g., IL-17 antibodies, such as secukinumab.

16 Claims, 8 Drawing Sheets

Specification includes a Sequence Listing.

(56) References Cited

OTHER PUBLICATIONS

The Merck Manual of Diagnosis & Therapy, "Diseases with associated psoriasis and scaling", 18th edition, Japanese Edition, 3rd impression of the first edition, 2007, pp. 1012-1016 [English Translation].
Nagoya University Press Release "(translation) Understanding of the pathogenesis of Generalized Pustular Psoriasis" [online] May 23, 2013, [searched on Mar. 14, 2017], Internet:URL:http://www.med.nagoya-u.ac.jp/medical/dbps_data/_material_/nu_medical/_res/topix/2013/Interleukin_2013522.pdf [English Translation].
Langley et al., "Secukinumab in Plaque Psoriasis—Results of Two Phase 3 Trials" New Eng J Med, 371;4, (Jul. 24, 2014).
Rich et al., "Secukinumab induction and maintenance therapy in moderate-to-severe plaque psoriasis: a randomized, double-blind, placebo-controlled, phase II regimen-finding study", The British Journal of Dermatology, vol. 168, No. 2, pp. 402-411, (Feb. 2013).
Robinson et al., "Treatment of Pustular psoriasis: From the medical board of the National Psoriasis Foundation", Journal of the American Academy of Dermatology, vol. 67, No. 2, pp. 279-288, Aug. 2012.
Daudén et al.,"Ustekinurnab: effective in a patient with severe recalcitrant generalized pustular psoriasis", The British Journal of Dermatology, vol. 163, No. 6, pp. 1346-1347, (Dec. 2010).
Senem Buyukkara Yilmaz et al., "Serum and tissue levels of IL-17 in different clinical subtypes of psoriasis", Archives of Dermatological Research; (founded in 1869 as Archiv für Dermatologie und Syphilis), vol. 304, No. 6, pp. 465-469, Mar. 20, 2012.
Yamamoto Masaaki et al., "Serum cytokines correlated with the disease severity of generalized pustular psoriasis", Disease Markers, vol. 34, No. 3, pp. 153-161, Mar. 2013.
Farber et al., "Pustular Psoriasis", Psoriasis, vol. 51, pp. 29-32, Jan. 1993.
Iizuka et al., "Pathophysiology of generalized pustular psoriasis", Arch Dermatol Res., vol. 295, S55-S59, 2003.
Iwatsuki et al. (2010) Clinical Guidelines for Generalized Pustular Psoriasis: Therapeutic Guides Incorporating Tumor Necrosis Factor-alpha Inhibitors; available on the website of the Japanese Dermatological Association at http://www.dermatol.or.jp/medical/guideline/pdf/nouhou_kansen.pdf (English Translation).
Lowes et al., "The IL-23/T17 pathogenic axis in psoriasis is amplified bt keratinocyte responses", Trends in immunology, vol. 34, No. 4, pp. 174-181, Apr. 2013.
Murakami et al., "Patients with palmoplantar pustulosis have increased IL-17 and IL-22 levels both in the lesion and serum", Experimental Dermtatology, Letter to the Editor, vol. 20, pp. 845-847, 2011.
Naldi et al., "The clinical spectrum of psoriasis", Clinics in Dermatology, vol. 25, pp. 510-518, 2007.
Sugiura et al., "The Majority of Generalized Pustular Psoriasis without Vulgaris is Caused by Deficiency of Interleukin-36 Receptor Antagonist", The Society for Investigative Dermatology, (Accepted Article Preview: Published ahead of advance online publication), pp. 1-29, 2013.
Teraki et al., "A case of generalized psoriasiform and pustular eruption induced by infliximab: evidence for skin-homing Th17 in the pathogenesis", British Associates of Dermatologists, vol. 163, pp. 1347-1351, 2010.
Umezawa et al., Therapeutic guidelines for the treatment of generalized pustular psoriasis (GPP) based on a proposed classification of disease severity, Arch Dermatol Res, vol. 295, pp. S43-S54, 2003.
"Ustekinumab: effective in a patient with severe recalcitrant generalized pustular psoriasis" British Jouranl of Dermatology, vol. 163, pp. 1346-1347, 2010.
Viguier et al., "Efficacy and Safety of Tumor Necrosis Factor Inhibitors in Acute Generalized Pustular Psoriasis", Arch Dermatol, vol. 148, No. 12, pp. 1423-1425, Dec. 2012 (Downloaded From: http://archderm.jamanetwork.com/ on May 21, 2013).
Yamamoto et al., "Serum cytokines correlated with the disease severity of generalized pustular psoriasis", Disease Markers, vol. 34, pp. 153-161, 2013.
Yilmaz et al., "Serum and tissue levels of IL-17 in diVerent clinical subtypes of psoriasis", Arch Dermatol Res, vol. 304, pp. 465-469, 2012.
Sugiura et al. The majority of generalized pustular psoriasis without psoriasis vulgaris is caused by deficiency of interleukin-36 receptor antagonist. J Invest Dermatol. Nov. 2013;133(11):2514-2521. Epub May 22, 2013.

\* cited by examiner

Fig. 2A  Erythema w/pustule
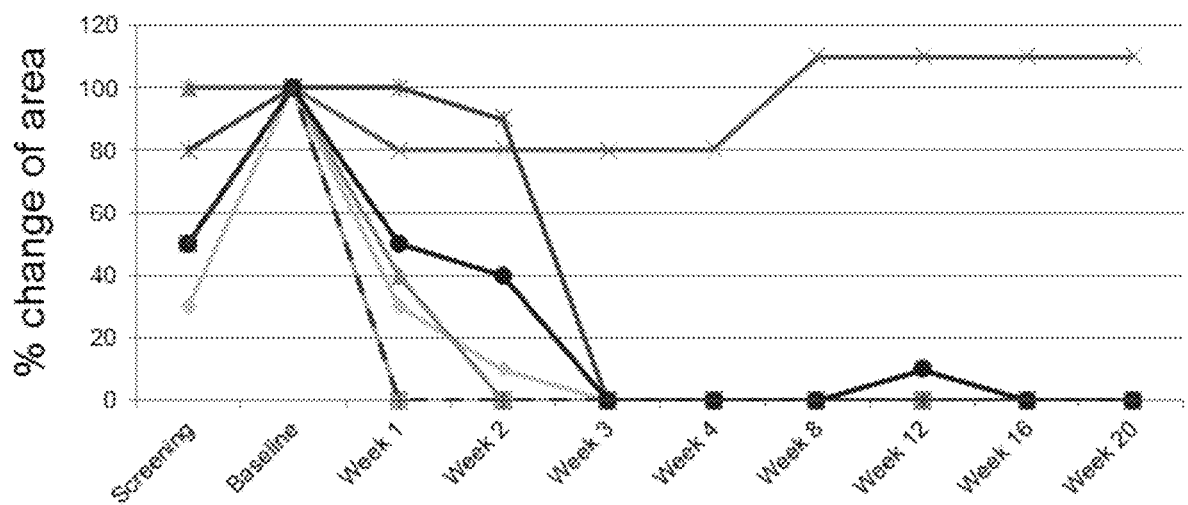

Fig. 2B  Erythema
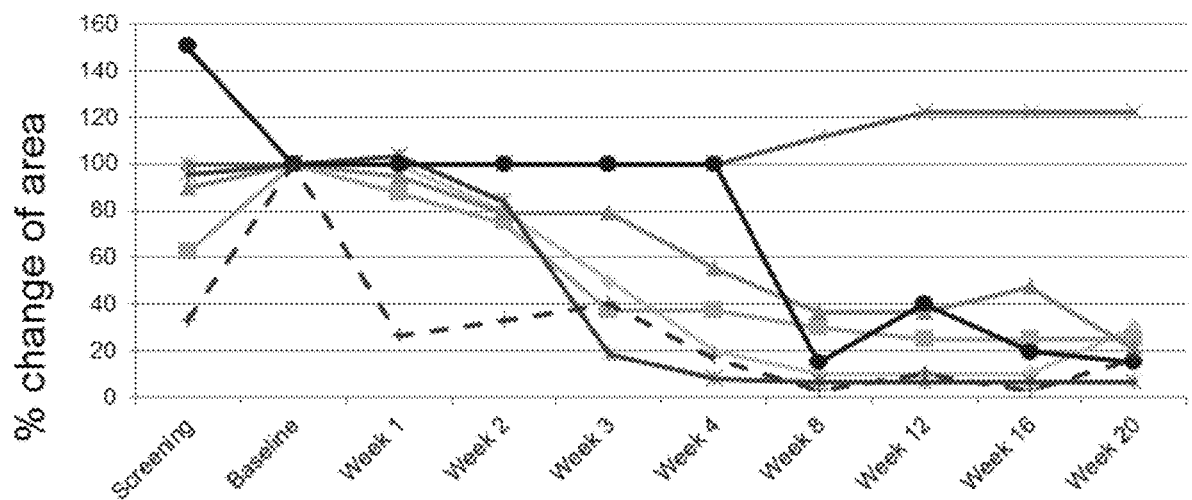

SEQUENCE LISTING

```
<160> NUMBER OF SEQ ID NOS: 17

<210> SEQ ID NO 1
<211> LENGTH: 5
<212> TYPE: PRT
<213> ORGANISM: artificial
<220> FEATURE:
<223> OTHER INFORMATION: CDR1 = hypervariable region 1 of heavy chain of
      AIN457

<400> SEQUENCE: 1

Asn Tyr Trp Met Asn
1               5

<210> SEQ ID NO 2
<211> LENGTH: 17
<212> TYPE: PRT
<213> ORGANISM: ARTIFICIAL
<220> FEATURE:
<223> OTHER INFORMATION: CDR2 = hypervariable region 2 of heavy chain of
      AIN457

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: ARTIFICIAL
<220> FEATURE:
<223> OTHER INFORMATION: CDR3 = hypervariable region 3 of heavy chain of
      AIN457

<400> SEQUENCE: 3

Asp Tyr Tyr Asp Ile Leu Thr Asp Tyr Tyr Ile His Tyr Trp Tyr Phe
1               5                   10                  15
```

Asp Leu

<210> SEQ ID NO 4
<211> LENGTH: 12
<212> TYPE: PRT
<213> ORGANISM: ARTIFICIAL
<220> FEATURE:
<223> OTHER INFORMATION: CDR1' = hypervariable region 1 of light chain
      of AIN457

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: ARTIFICIAL
<220> FEATURE:
<223> OTHER INFORMATION: CDR2' = hypervariable region 2 of light chain
      AIN457

<400> SEQUENCE: 5

Gly Ala Ser Ser Arg Ala Thr
1               5

<210> SEQ ID NO 6
<211> LENGTH: 9
<212> TYPE: PRT
<213> ORGANISM: ARTIFICIAL
<220> FEATURE:
<223> OTHER INFORMATION: CDR3' = hypervariable region 3 of light chain
      AIN457

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: HOMO SAPIENS
<220> FEATURE:
<221> NAME/KEY: CDS
<222> LOCATION: (1)..(381)

<400> SEQUENCE: 7

```
gag gtg cag ttg gtg gag tct ggg gga ggc ttg gtc cag cct ggg ggg       48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agt aac tat       96
Ser Leu Arg Leu Ser Cys Ala Ala Ser Gly Phe Thr Phe Ser Asn Tyr
            20                  25                  30 tgg atg aac tgg gtc cgc cag gct cca ggg aaa ggg ctg gag tgg gtg      144
Trp Met Asn Trp Val Arg Gln Ala Pro Gly Lys Gly Leu Glu Trp Val
        35                  40                  45 gcc gcc ata aac caa gat gga agt gag aaa tac tat gtg ggc tct gtg      192
Ala Ala Ile Asn Gln Asp Gly Ser Glu Lys Tyr Tyr Val Gly Ser Val
    50                  55                  60 aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
65                  70                  75                  80 ctg caa atg aac agc ctg aga gtc gag gac acg gct gtg tat tac tgt      288
Leu Gln Met Asn Ser Leu Arg Val Glu Asp Thr Ala Val Tyr Tyr Cys
                85                  90                  95
```

| | | |
|---|---|---|
| gtg agg gac tat tac gat att ttg acc gat tat tac atc cac tat tgg<br>Val Arg Asp Tyr Tyr Asp Ile Leu Thr Asp Tyr Tyr Ile His Tyr Trp<br>100 105 110 | | 336 |
| tac ttc gat ctc tgg ggc cgt ggc acc ctg gtc act gtc tcc tca<br>Tyr Phe Asp Leu Trp Gly Arg Gly Thr Leu Val Thr Val Ser Ser<br>115 120 125 | | 381 |

<210> SEQ ID NO 8
<211> LENGTH: 127
<212> TYPE: PRT
<213> ORGANISM: HOMO SAPIENS

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 9
<211> LENGTH: 327
<212> TYPE: DNA
<213> ORGANISM: HOMO SAPIENS
<220> FEATURE:
<221> NAME/KEY: CDS
<222> LOCATION: (1)..(327)

<400> SEQUENCE: 9

| | | |
|---|---|---|
| gaa att gtg ttg acg cag tct cca ggc acc ctg tct ttg tct cca ggg<br>Glu Ile Val Leu Thr Gln Ser Pro Gly Thr Leu Ser Leu Ser Pro Gly<br>1               5                   10                  15 | | 48 |
| gaa aga gcc acc ctc tcc tgc agg gcc agt cag agt gtt agc agc agc<br>Glu Arg Ala Thr Leu Ser Cys Arg Ala Ser Gln Ser Val Ser Ser Ser<br>            20                  25                  30 | | 96 |
| tac tta gcc tgg tac cag cag aaa cct ggc cag gct ccc agg ctc ctc<br>Tyr Leu Ala Trp Tyr Gln Gln Lys Pro Gly Gln Ala Pro Arg Leu Leu<br>        35                  40                  45 | | 144 |
| atc tat ggt gca tcc agc agg gcc act ggc atc cca gac agg ttc agt<br>Ile Tyr Gly Ala Ser Ser Arg Ala Thr Gly Ile Pro Asp Arg Phe Ser<br>    50                  55                  60 | | 192 |
| ggc agt ggg tct ggg aca gac ttc act ctc acc atc agc aga ctg gag<br>Gly Ser Gly Ser Gly Thr Asp Phe Thr Leu Thr Ile Ser Arg Leu Glu<br>65                  70                  75                  80 | | 240 |
| cct gaa gat ttt gca gtg tat tac tgt cag cag tat ggt agc tca ccg<br>Pro Glu Asp Phe Ala Val Tyr Tyr Cys Gln Gln Tyr Gly Ser Ser Pro<br>                85                  90                  95 | | 288 |
| tgc acc ttc ggc caa ggg aca cga ctg gag att aaa cga<br>Cys Thr Phe Gly Gln Gly Thr Arg Leu Glu Ile Lys Arg<br>            100                 105 | | 327 |

<210> SEQ ID NO 10
<211> LENGTH: 109
<212> TYPE: PRT
<213> ORGANISM: HOMO SAPIENS

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105

<210> SEQ ID NO 11
<211> LENGTH: 10
<212> TYPE: PRT
<213> ORGANISM: artificial
<220> FEATURE:
<223> OTHER INFORMATION: CDR1-x = hypervariable domain x of heavy chain
      of AIN457

<400> SEQUENCE: 11

Gly Phe Thr Phe Ser Asn Tyr Trp Met Asn
1               5                   10

<210> SEQ ID NO 12
<211> LENGTH: 11
<212> TYPE: PRT
<213> ORGANISM: artificial
<220> FEATURE:
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr
1               5                   10

<210> SEQ ID NO 13
<211> LENGTH: 23
<212> TYPE: PRT
<213> ORGANISM: ARTIFICIAL
<220> FEATURE:
<223> OTHER INFORMATION: CDR3-x = hypervariable domain x of heavy chain
      AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20

<210> SEQ ID NO 14
<211> LENGTH: 711
<212> TYPE: DNA
<213> ORGANISM: homo sapiens

```
<220> FEATURE:
<221> NAME/KEY: CDS
<222> LOCATION: (1)..(708)

<400> SEQUENCE: 14 acc atg gaa acc cca gcg gag ctt ctc ttc ctc ctg cta ctc tgg ctc      48
Thr Met Glu Thr Pro Ala Glu Leu Leu Phe Leu Leu Leu Leu Trp Leu
1               5                   10                  15 cca gat acc acc gga gaa att gtg ttg acg cag tct cca ggc acc ctg      96
Pro Asp Thr Thr Gly Glu Ile Val Leu Thr Gln Ser Pro Gly Thr Leu
            20                  25                  30 tct ttg tct cca ggg gaa aga gcc acc ctc tcc tgc agg gcc agt cag     144
Ser Leu Ser Pro Gly Glu Arg Ala Thr Leu Ser Cys Arg Ala Ser Gln
        35                  40                  45 agt gtt agc agc agc tac tta gcc tgg tac cag cag aaa cct ggc cag     192
Ser Val Ser Ser Ser Tyr Leu Ala Trp Tyr Gln Gln Lys Pro Gly Gln
    50                  55                  60 gct ccc agg ctc ctc atc tat ggt gca tcc agc agg gcc act ggc atc     240
Ala Pro Arg Leu Leu Ile Tyr Gly Ala Ser Ser Arg Ala Thr Gly Ile
65                  70                  75                  80 cca gac agg ttc agt ggc agt ggg tct ggg aca gac ttc act ctc acc     288
Pro Asp Arg Phe Ser Gly Ser Gly Ser Gly Thr Asp Phe Thr Leu Thr
                85                  90                  95 atc agc aga ctg gag cct gaa gat ttt gca gtg tat tac tgt cag cag     336
Ile Ser Arg Leu Glu Pro Glu Asp Phe Ala Val Tyr Tyr Cys Gln Gln
            100                 105                 110 tat ggt agc tca ccg tgc acc ttc ggc caa ggg aca cga ctg gag att     384
Tyr Gly Ser Ser Pro Cys Thr Phe Gly Gln Gly Thr Arg Leu Glu Ile
        115                 120                 125 aaa cga act gtg gct gca cca tct gtc ttc atc ttc ccg cca tct gat     432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac     480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc     528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac     576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac     624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc     672
Glu Lys His Lys Val Tyr Ala Cys Glu Val Thr His Gln Gly Leu Ser
    210                 215                 220 tcg ccc gtc aca aag agc ttc aac agg gga gag tgt tag                 711
Ser Pro Val Thr Lys Ser Phe Asn Arg Gly Glu Cys
225                 230                 235

<210> SEQ ID NO 15
<211> LENGTH: 236
<212> TYPE: PRT
<213> ORGANISM: homo sapiens

<400> SEQUENCE: 15

Thr Met Glu Thr Pro Ala Glu Leu Leu Phe Leu Leu Leu Leu Trp Leu
1               5                   10                  15

Pro Asp Thr Thr Gly Glu Ile Val Leu Thr Gln Ser Pro Gly Thr Leu
            20                  25                  30
```

```
Ser Leu Ser Pro Gly Glu Arg Ala Thr Leu Ser Cys Arg Ala Ser Gln
         35                  40                  45

Ser Val Ser Ser Tyr Leu Ala Trp Tyr Gln Gln Lys Pro Gly Gln
 50                  55                  60

Ala Pro Arg Leu Leu Ile Tyr Gly Ala Ser Ser Arg Ala Thr Gly Ile
 65                  70                  75                  80

Pro Asp Arg Phe Ser Gly Ser Gly Ser Gly Thr Asp Phe Thr Leu Thr
                 85                  90                  95

Ile Ser Arg Leu Glu Pro Glu Asp Phe Ala Val Tyr Tyr Cys Gln Gln
                100                 105                 110

Tyr Gly Ser Ser Pro Cys Thr Phe Gly Gln Gly Thr Arg Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 16
<211> LENGTH: 783
<212> TYPE: DNA
<213> ORGANISM: homo sapiens
<220> FEATURE:
<221> NAME/KEY: CDS
<222> LOCATION: (1)..(780)

<400> SEQUENCE: 16 acc atg gaa ttg ggg ctg agc tgg gtt ttc ctt gtt gct att tta gaa      48
Thr Met Glu Leu Gly Leu Ser Trp Val Phe Leu Val Ala Ile Leu Glu
 1               5                  10                  15 ggt gtc cac tgt gag gtg cag ttg gtg gag tct ggg gga ggc ttg gtc     96
Gly Val His Cys Glu Val Gln Leu Val Glu Ser Gly Gly Gly Leu Val
             20                  25                  30 cag cct ggg ggg tcc ctg aga ctc tcc tgt gca gcc tct gga ttc acc    144
Gln Pro Gly Gly Ser Leu Arg Leu Ser Cys Ala Ala Ser Gly Phe Thr
         35                  40                  45 ttt agt aac tat tgg atg aac tgg gtc cgc cag gct cca ggg aaa ggg    192
Phe Ser Asn Tyr Trp Met Asn Trp Val Arg Gln Ala Pro Gly Lys Gly
 50                  55                  60 ctg gag tgg gtg gcc gcc ata aac caa gat gga agt gag aaa tac tat    240
Leu Glu Trp Val Ala Ala Ile Asn Gln Asp Gly Ser Glu Lys Tyr Tyr
 65                  70                  75                  80 gtg ggc tct gtg aag ggc cga ttc acc atc tcc aga gac aac gcc aag    288
Val Gly Ser Val Lys Gly Arg Phe Thr Ile Ser Arg Asp Asn Ala Lys
                 85                  90                  95 aac tca ctg tat ctg caa atg aac agc ctg aga gtc gag gac acg gct    336
Asn Ser Leu Tyr Leu Gln Met Asn Ser Leu Arg Val Glu Asp Thr Ala
                100                 105                 110
```

```
                                                    -continued gtg tat tac tgt gtg agg gac tat tac gat att ttg acc gat tat tac        384
Val Tyr Tyr Cys Val Arg Asp Tyr Tyr Asp Ile Leu Thr Asp Tyr Tyr
        115                 120                 125 atc cac tat tgg tac ttc gat ctc tgg ggc cgt ggc acc ctg gtc act        432
Ile His Tyr Trp Tyr Phe Asp Leu Trp Gly Arg Gly Thr Leu Val Thr
        130                 135                 140 gtc tcc tca gcc tcc acc aag ggc cca tcg gtc ttc ccc ctg gca ccc        480
Val Ser Ser Ala Ser Thr Lys Gly Pro Ser Val Phe Pro Leu Ala Pro
145                 150                 155                 160 tcc tcc aag agc acc tct ggg ggc aca gcg gcc ctg ggc tgc ctg gtc        528
Ser Ser Lys Ser Thr Ser Gly Gly Thr Ala Ala Leu Gly Cys Leu Val
                165                 170                 175 aag gac tac ttc ccc gaa ccg gtg acg gtg tcg tgg aac tca ggc gcc        576
Lys Asp Tyr Phe Pro Glu Pro Val Thr Val Ser Trp Asn Ser Gly Ala
            180                 185                 190 ctg acc agc ggc gtg cac acc ttc ccg gct gtc cta cag tcc tca gga        624
Leu Thr Ser Gly Val His Thr Phe Pro Ala Val Leu Gln Ser Ser Gly
        195                 200                 205 ctc tac tcc ctc agc agc gtg gtg acc gtg ccc tcc agc agc ttg ggc        672
Leu Tyr Ser Leu Ser Ser Val Val Thr Val Pro Ser Ser Ser Leu Gly
        210                 215                 220 acc cag acc tac atc tgc aac gtg aat cac aag ccc agc aac acc aag        720
Thr Gln Thr Tyr Ile Cys Asn Val Asn His Lys Pro Ser Asn Thr Lys
225                 230                 235                 240 gtg gac aag aga gtt gag ccc aaa tct tgt gac aaa act cac aca tgc        768
Val Asp Lys Arg Val Glu Pro Lys Ser Cys Asp Lys Thr His Thr Cys
                245                 250                 255 cca ccg tgc cca taa                                                     783
Pro Pro Cys Pro
            260

<210> SEQ ID NO 17
<211> LENGTH: 260
<212> TYPE: PRT
<213> ORGANISM: homo sapiens

<400> SEQUENCE: 17

Thr Met Glu Leu Gly Leu Ser Trp Val Phe Leu Val Ala Ile Leu Glu
1               5                   10                  15

Gly Val His Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Trp Met Asn Trp Val Arg Gln Ala Pro Gly Lys Gly
    50                  55                  60

Leu Glu Trp Val Ala Ala Ile Asn Gln Asp Gly Ser Glu Lys Tyr Tyr
65                  70                  75                  80

Val Gly Ser Val Lys Gly Arg Phe Thr Ile Ser Arg Asp Asn Ala Lys
                85                  90                  95

Asn Ser Leu Tyr Leu Gln Met Asn Ser Leu Arg Val Glu Asp Thr Ala
            100                 105                 110

Val Tyr Tyr Cys Val Arg Asp Tyr Tyr Asp Ile Leu Thr Asp Tyr Tyr
        115                 120                 125

Ile His Tyr Trp Tyr Phe Asp Leu Trp Gly Arg Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
```

-continued

```
                165                 170                 175
Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
            210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro
            260
```

METHODS OF TREATING PALMOPLANTAR PUSTULAR PSORIASIS (PPP) USING IL-17 ANTIBODY

RELATED APPLICATIONS

The instant application is a continuation of U.S. patent application Ser. No. 14/911,387, now U.S. Pat. No. 10,434,172, which claims priority to U.S. Provisional Patent application No. 61/886,242, filed Aug. 15, 2013, which is incorporated by reference in its entirety.

TECHNICAL FIELD

The disclosure is directed to methods, treatment regimens, uses, kits and therapies for treating Generalized Pustular Psoriasis (GPP) by employing IL-17 antagonists, e.g., IL-17 antibodies.

BACKGROUND OF THE DISCLOSURE

Psoriasis is a chronic relapsing disease of the skin characterized by variable clinical features. The lesions are classified as erythrosquamous, which indicates that both the vasculature (erythema) and the epidermis (increased scale formation) are involved. Pustular psoriasis is a variant of psoriasis with sterile pustules presenting locally or broadly on the skin either acutely, subacutely, or chronically (Camp, RDR (1998) Pustular forms of psoriasis. Textbook of Dermatology, Champion, R H et al eds, Blackwell Science, Oxford; 1633-43). Pustular psoriasis is frequently categorized as either generalized pustular psoriasis (GPP) or localized pustular psoriasis (Farber and Nall (1993) Cutis 51:29-32). In generalized pustular psoriasis, sterile pustules can cover almost the entire body, and in the localized form, pustules are confined to isolated locations. GPP includes von Zumbusch (acute GPP), generalized form of acrodermatitis continua (Hallopeau), acute exanthematic, GPP of pregnancy (impetigo herpetiformis), infantile and juvenile GPP, and circinate and annular GPP, whilst localized pustular psoriasis includes chronic and acute palmoplantar pustulosis. (Farber and Nall, supra; Iizuka et al (2003) Arch Dermatol Res 295:S55-S59).

GPP is a rare form of psoriasis that usually presents as numerous aseptic pustules occurring on reddened skin over the whole body and is a potentially life-threatening systemic inflammatory disease. It is frequently associated with fever, and involves the formation of subcorneal pustules histopathologically characterized by Kogoj's spongiform pustules. It is characterized by recurrence in periodic episodes. In the course of the disease, GPP patients may have laboratory abnormalities associated with systemic inflammation response, frequently complicated with mucosal symptoms and arthritis, and less frequently with respiratory failure, eye disease, or secondary amyloidosis. GPP can be preceded by psoriasis vulgaris (PV). However, this is not always the case, and recent research shows that GPP that is not preceeded by PV is a distinct subtype of GPP, distinguishable from GPP with PV by a deficiency in the Interleukin 36 Receptor Antagonist (DITRA) due to mutations in IL36RN. (Sugiura et al. (2013) J. Investi. Derm. Accepted article preview 22 May 2013 (doi:10.1038/jid.2013.230)).

A "pustular psoriasis (generalized type) clinical practice guideline" has been published by the Japanese Dermatological Association (Iwatsuki K, Terui M, Ozawa A, et al. (2010) Clinical Guidelines for Generalized Pustular Psoriasis: Therapeutic Guides Incorporating Tumor Necrosis Factor-alpha Inhibitors), presenting information about the diagnosis and the severity criteria of GPP and recommending therapeutic guides for GPP, as an outcome of a "surveillance study on a rare intractable skin disorder" of the Japan Ministry of Health Labor Welfare (MHLW) Intractable Disease Conquest Research Program. In the guideline, systemic corticosteroids, ciclosporin, etretinate, methotrexate (MTX), and infliximab are recommended as the treatment for GPP. Infliximab, and other biologic drugs targeting TNF-α, have shown some treatment success (see, e.g., Viguier et al. (2012) Arch Dermatol 148:1423-25), as has ustekinumab (see, e.g., Dauden (2010) Br. J. Derm. 163: 1346-68). However, only three drugs (ciclosporin, etretinate, and infliximab) are approved for use in the treatment of pustular psoriasis, and these drugs all have significant limitations. For example, systemic long-term corticosteroids cause Cushing's syndrome and hypertension, amongst other side effects. Methotrexate has well-known liver and hematology toxicity. Ciclosporin may be restricted due to its nephrotoxicity after chronic administration. Etretinate has a very long half-life (about 100 days) and is associated with teratogenicity. Moreover, the oral cavity symptom (including dryness of the mucosa) caused by etretinate often prevents the continuation of its treatment. For infliximab, it is reported that there is loss of response due to the development of neutralizing antibodies (Asahina A (2012) Biologics. Diagnosis, Understanding and Treatment Dermatology Clinical Asset 10 Current Understanding of the Pathology and Treatment of Psoriasis; Tokyo: Nakayamashoten, 264-8), and TNF alpha antagonists have the potential to reactivate tuberculosis.

There are fewer therapeutic options available for GPP than for plaque psoriasis, and those that are available have significant limitations. Hence, broadening the options for the treatment of GPP would address a high unmet medical need.

BRIEF SUMMARY OF THE DISCLOSURE

IL-17A is the central lymphokine of a newly defined subset of inflammatory T cells, the Th17 cells, which are pivotal in several autoimmune and inflammatory processes. IL-17A neutralization is expected to treat the underlying pathophysiology of immune mediated disease, and as a consequence provide relief of symptoms. IL-17A is considered to activate neutrophils, and hence might play an important role in pustular psoriasis, since the presence of neutrophils in pustules is a typical feature of this disease. It has been shown that IL-17 is highly expressed in the skin tissue of patients with severe PV and pustular psoriasis, including both palmoplantar and GPP subgroups (Yilmaz et al. (2012) Arch. Dermatol. Res 304:465-69). However, Yamamoto et al. report that, while increased levels of IL-17 in GPP patient's serum is associated with an increased level of the general inflammatory marker CRP, this increase is not associated with GPP score or levels of white blood cells (Yamamoto et al. (2013) Disease Markers 34:153-61). Thus, the role of IL-7 in GPP is not fully understood.

Secukinumab (AIN457) is a high-affinity fully human monoclonal anti-human antibody that inhibits IL-17A activity, which has emerged as a potential treatment for patients with various autoimmune diseases, e.g., rheumatoid arthritis, ankylosing spondylitis, psoriatic arthritis, diabetes, asthma, chronic plaque-type psoriasis, and multiple sclerosis. Several Phase II and III studies have shown that secukinumab is superior to placebo in achievement of PASI 75 in treating chronic plaque-type psoriasis (e.g., secukinumab 3×150 mg and 3×75 mg were both superior to placebo in achievement of PASI 75 at Week 12 (81.5% and 57.1%, respectively, vs. 9.1%) in study CAIN457A2220. Secukinumab is currently used in global Phase III studies for the treatment of chronic plaque-type psoriasis, and has again shown superiority over placebo, and newly also over etanercept. International Patent Publication WO2012/045848 provides dosing regimens for the use of secukinumab to treat psoriasis, but makes no mention of GPP.

Disclosed herein are methods of treating Generalized Pustular Psoriasis (GPP), comprising administering to a patient in need thereof an IL-17 antibody or antigen binding fragment thereof, wherein the IL-17 antibody or antigen binding fragment binds to an epitope of an IL-17 homodimer having two mature human IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 antibody or antigen binding fragment thereof has a $K_D$ of about 100-about 200 pM (e.g., as determined by Biacore®), and wherein the IL-17 antibody or antigen binding fragment thereof has an in vivo half-life of about 23-about 30 days.

Disclosed herein are methods of treating GPP, comprising subcutaneously administering an IL-17 antibody or antigen binding fragment thereof to a patient in need thereof as a dose of about 150 mg-about 300 mg with initial dosing at weeks 0, 1, 2 and 3, followed by monthly dosing, starting at week 4.

Disclosed herein are methods of treating GPP, comprising: a) subcutaneously administering an IL-17 antibody or antigen binding fragment thereof to a patient in need thereof at a dose of about 150 mg during weeks 0, 1, 2, 3, and 4; and b) thereafter, subcutaneously administering the IL-17 antibody or antigen binding fragment thereof to the patient at a dose of about 300 mg during week 8, 9, and 12 and then monthly thereafter, beginning during week 16.

Disclosed herein are methods of treating GPP, comprising: a) subcutaneously administering an IL-17 antibody or antigen binding fragment thereof to a patient in need thereof at a dose of about 150 mg during weeks 0, 1, 2, 3, and 4; b) assigning the patient to a treatment assessment based on clinical components of a CGI evaluation administered during week 8, wherein assigning a treatment assessment "very much improved" or "much improved" provides an indication that no up-titration is required, and wherein assigning a treatment assessment "worse", "no change" or "minimally improved" provides an indication that up-titration is required; and c) i) thereafter, subcutaneously administering the IL-17 antibody or antigen binding fragment thereof to the patient at a dose of about 150 mg monthly, beginning during week 8, if no up-titration is required; or ii) thereafter, subcutaneously administering the IL-17 antibody or antigen binding fragment thereof to the patient at a dose of about 300 mg during weeks 8, 9 and 12 and then monthly thereafter, beginning during week 16, if up-titration is required.

Disclosed herein are kits for the treatment of a patient having GPP, comprising: a) a pharmaceutical composition comprising a therapeutically effective amount of an IL-17 antibody or antigen binding fragment thereof; b) means for administering the IL-17 antibody or antigen binding fragment thereof to the patient; and c) instructions providing: i) subcutaneously administering the IL-17 antibody or antigen binding fragment thereof to the patient at a dose of about 150 mg during weeks 0, 1, 2, 3, and 4; ii) I) thereafter, subcutaneously administering the IL-17 antibody or antigen binding fragment thereof to the patient at a dose of about 150 mg monthly, beginning during week 8; or II) thereafter, subcutaneously administering the IL-17 antibody or antigen binding fragment thereof to the patient at a dose of about 300 mg during weeks 8, 9 and 12 and then monthly thereafter, beginning during week 16.

Disclosed herein are kits for the treatment of a patient having GPP, comprising: a) a pharmaceutical composition comprising a therapeutically effective amount of an IL-17 antibody or antigen binding fragment thereof; b) means for administering the IL-17 antibody or antigen binding fragment thereof to the patient; and c) instructions providing: i) subcutaneously administering the IL-17 antibody or antigen binding fragment thereof to the patient at a dose of about 150 mg during weeks 0, 1, 2, 3, and 4; ii) assigning the patient to a treatment assessment based on clinical components of a CGI evaluation administered during week 8, wherein assigning a treatment assessment "very much improved" or "much improved" provides an indication that no up-titration is required, and wherein assigning a treatment assessment "worse", "no change" or "minimally improved" provides an indication that up-titration is required; and iii) I) thereafter, subcutaneously administering the IL-17 antibody or antigen binding fragment thereof to the patient at a dose of about 150 mg monthly, beginning during week 8, if no up-titration is required; or II) thereafter, subcutaneously administering the IL-17 antibody or antigen binding fragment thereof to the patient at a dose of about 300 mg during weeks 8, 9 and 12 and then monthly thereafter, beginning during week 16, if up-titration is required.

Disclosed herein are IL-17 antibodies or antigen binding fragments thereof for use in treating Generalized Pustular Psoriasis (GPP) in a patient in need thereof, characterized in that the IL-17 antibody or antigen binding fragment thereof binds to an epitope of an IL-17 homodimer having two mature human IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 antibody or antigen binding fragment thereof has a KD of about 100-about 200 pM (e.g., as determined by Biacore®), and wherein the IL-17 antibody or antigen binding fragment thereof has an in vivo half-life of about 23-about 30 days Disclosed herein are IL-17 antibodies or antigen binding fragments thereof for use in treating GPP in a patient in need thereof, characterized in that the IL-17 antibody or antigen binding fragment thereof is to be subcutaneously administered to the patient as a dose of about 150 mg-about 300 mg with initial dosing at weeks 0, 1, 2 and 3, followed by monthly dosing starting at week 4.

Disclosed herein are IL-17 antibodies or antigen binding fragments thereof for use in treating GPP in a patient in need thereof, characterized in that the IL-17 antibody or antigen binding fragment thereof is to be administered to the patient: a) subcutaneously at a dose of about 150 mg during weeks 0, 1, 2, 3, and 4; and b) thereafter, subcutaneously at a dose of about 300 mg during week 8, 9, and 12 and then monthly thereafter, beginning during week 16.

Disclosed herein are IL-17 antibodies or antigen binding fragments thereof for use in treating GPP in a patient in need thereof, characterized in that the IL-17 antibody or antigen binding fragment thereof is to be administered to the patient: a) subcutaneously at a dose of about 150 mg during weeks 0, 1, 2, 3, and 4; b) i) thereafter, subcutaneously at a dose of about 150 mg monthly, beginning during week 8, if no up-titration is required; or ii) thereafter, subcutaneously at a dose of about 300 mg during weeks 8, 9 and 12 and then monthly thereafter, beginning during week 16, if up-titration is required, wherein prior to step b), the patient is assigned to a treatment assessment based on clinical components of a CGI evaluation administered during week 8, wherein assigning a treatment assessment "very much improved" or "much improved" provides an indication that no up-titration is required, and wherein assigning a treatment assessment "worse", "no change" or "minimally improved" provides an indication that up-titration is required. In preferred embodiments, the disclosed methods, kits and uses employ an IL-17 antibody (e.g., secukinumab or ixekizumab), e.g., a human or humanized antibody, most preferably secukinumab.

Additionally disclosed are improved methods for treating plaque-type psoriasis that utilize up-titration and down-titration of the IL-17 antagonist, e.g., an IL-17 antibody, such as secukinumab, as well as modification of dose frequency. Further disclosed are methods of treating palmoplantar pustular psoriasis using the disclosed IL-17 antagonists, e.g., IL-17 antibodies, such as secukinumab.

Additional methods, regimens, uses, and kits are provided in the following description and appended claims. Further features, advantages and aspects of the present disclosure will become apparent to those skilled in the art from the following description and appended claims.

BRIEF DESCRIPTION OF THE DRAWINGS

FIG. 2A shows the percent of the body surface area affected with erythema with pustules for several patients treated with secukinumab in study CAIN457A1302; the symptoms at baseline (BSL) are set as 100%. Note that treatment with secukinumab is capable of reducing the severity of the key symptom of GPP in a majority of patients. Each line in FIG. 2A represents an individual patient profile.

FIG. 2B shows the percent of the body surface area affected with erythema. Note that treatment with secukinumab is capable of reducing the severity of this key symptom of psoriasis in a majority of patients. Each line in FIG. 2B represents an individual patient profile.

DETAILED DESCRIPTION OF THE DISCLOSURE

Figure 1:
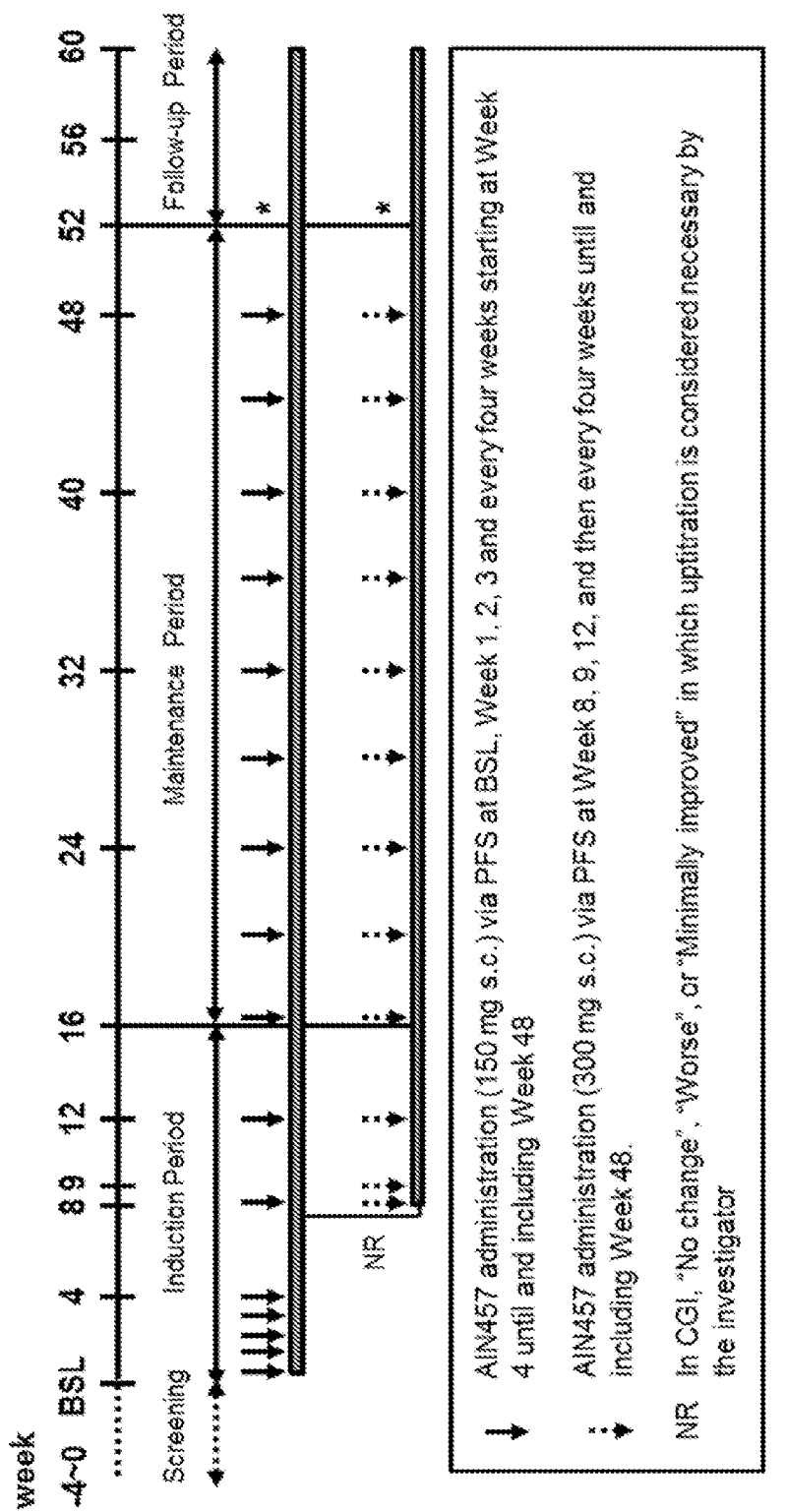
FIG. 1: Provides the clinical trial design for CAIN457A1302.

The term "comprising" encompasses "including" as well as "consisting," e.g. a composition "comprising" X may consist exclusively of X or may include something additional, e.g., X+Y.

The term "about" in relation to a numerical value x means +/−10% unless the context dictates otherwise.

By "monthly" is meant about every 4 weeks (e.g., every 4 weeks), which is about every 28 days (e.g., every 28 days).

The term "antibody" as referred to herein includes whole antibodies and any antigen-binding portion or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some embodiments of the disclosed methods, regimens, kits, processes, uses and compositions, an antibody to IL-17 or the IL-17 receptor is employed, preferably an antibody to IL-17, e.g., secukinumab.

The term "antigen-binding portion" of an antibody as used herein, refers to fragments of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Exemplary antigen binding sites include the CDRs of secukinumab as set forth in SEQ ID NOs:1-6 and 11-13 (Table 4), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art. In some embodiments of the disclosed methods, regimens, kits, processes, uses and compositions, a single chain antibody or an antigen-binding portion of an antibody against IL-17 (e.g., secukinumab) or the IL-17 receptor is employed.

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed methods, regimens, kits, processes, uses and compositions, the IL-17 antibody is a human antibody, an isolated antibody, and/or a monoclonal antibody.

The term "IL-17" refers to IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

The term "$K_D$" is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. In some embodiments, the IL-17 antibody or antigen binding fragment thereof binds human IL-17 with a $K_D$ of about 100-250 pM (as measured by Biacore®).

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore® analysis.

As used herein, the terms "subject" and "patient" include any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

An antibody that "inhibits" one or more of these IL-17 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity affects a statistically significant decrease, e.g., by at least about 10% of the measured parameter, by at least 50%, 80% or 90%, and in certain embodiments of the disclosed methods, uses, processes, kits and compositions, the IL-17 antibody used may inhibit greater than 95%, 98% or 99% of IL-17 functional activity.

"Inhibit IL-6" as used herein refers to the ability of an IL-17 antibody (e.g., secukinumab) to decrease IL-6 production from primary human dermal fibroblasts. The production of IL-6 in primary human (dermal) fibroblasts is dependent on IL-17 (Hwang et al., (2004) Arthritis Res Ther; 6:R120-128). In short, human dermal fibroblasts are stimulated with recombinant IL-17 in the presence of various concentrations of an IL-17 binding molecule or human IL-17 receptor with Fc part. The chimeric anti-CD25 antibody Simulect® (basiliximab) may be conveniently used as a negative control. Supernatant is taken after 16 h stimulation and assayed for IL-6 by ELISA. An IL-17 antibody or antigen binding fragment thereof as disclosed herein typically has an $IC_{50}$ for inhibition of IL-6 production (in the presence 1 nM human IL-17) of about 50 nM or less (e.g., from about 0.01 to about 50 nM) when tested as above, i.e., said inhibitory activity being measured on IL-6 production induced by hu-IL-17 in human dermal fibroblasts. In some embodiments of the disclosed methods, regimens, kits, processes, uses and compositions, the IL-17 antibody or antigen binding fragment thereof, e.g., secukinumab, and functional derivatives thereof have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

The term "derivative", unless otherwise indicated, is used to define amino acid sequence variants, and covalent modifications (e.g., pegylation, deamidation, hydroxylation, phosphorylation, methylation, etc.) of an IL-17 antibody or antigen binding fragment thereof, e.g., secukinumab, according to the present disclosure, e.g., of a specified sequence (e.g., a variable domain). A "functional derivative" includes a molecule having a qualitative biological activity in common with the disclosed IL-17 antibodies or antigen binding fragments thereof. A functional derivative includes fragments and peptide analogs of an IL-17 antibody or antigen binding fragment thereof as disclosed herein. Fragments comprise regions within the sequence of a polypeptide according to the present disclosure, e.g., of a specified sequence. Functional derivatives of the IL-17 antibodies or antigen binding fragments thereof disclosed herein (e.g., functional derivatives of secukinumab) preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-17 binding molecules disclosed herein (e.g., the $V_H$ and/or $V_L$ sequences of Table 4), and substantially retain the ability to bind human IL-17 or, e.g., inhibit IL-6 production of IL-17 induced human dermal fibroblasts.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this application. In some embodiments, the sequence identity of a derivative IL-17 antibody (e.g., a derivative of secukinumab, e.g., a secukinumab biosimilar antibody) can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of a polypeptide according to the present disclosure, e.g., of a specified sequence, still have the ability to bind the human IL-17 or, e.g., inhibit IL-6 production of IL-17 induced human dermal fibroblasts. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "pharmaceutically acceptable" means a non-toxic material that does not interfere with the effectiveness of the biological activity of the active ingredient(s).

The term "administering" in relation to a compound, e.g., an IL-17 binding molecule or another agent, is used to refer to delivery of that compound to a patient by any route.

As used herein, a "therapeutically effective amount" refers to an amount of an IL-17 antibody or antigen binding fragment thereof, e.g., secukinumab, that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., an IL-17 antibody, e.g., secukinumab) administered alone, the term refers to that ingredient alone. When applied to a combination, the term refers to combined amounts of the active ingredients that result in the therapeutic effect, whether administered in combination, serially or simultaneously.

The term "treatment" or "treat" refer to both prophylactic or preventative treatment as well as curative or disease modifying treatment, including treatment of a patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment.

The phrase "therapeutic regimen" means the regimen used to treat an illness, e.g., the dosing protocol used during the treatment of GPP. A therapeutic regimen may include an induction regimen and a maintenance regimen.

The phrase "induction regimen" or "induction period" refers to a treatment regimen (or the portion of a treatment regimen) that is used for the initial treatment of a disease. In some embodiments, the disclosed methods, uses, kits, processes and regimens (e.g., methods of treating GPP) employ an induction regimen. During the treatment of GPP, the first 12 weeks of treatment is generally referred to as the "induction period", and it is during this time that an induction regimen is employed. While 12 weeks is a traditional induction period for psoriasis treatment, an induction period may be as short as the first 4 weeks of treatment, or as long as the first 16 weeks of treatment. In some cases, the induction period is the period until maximum efficacy is reached. The general goal of an induction regimen is to provide a high level of drug to a patient during the initial period of a treatment regimen. An induction regimen may employ (in part or in whole) a "loading regimen", which may include administering a greater dose of the drug than a physician would employ during maintenance regimen, administering a drug more frequently than a physician would administer the drug during a maintenance regimen, or both. Dose escalation may occur during or after an induction regimen.

The phrase "maintenance regimen" or "maintenance period" refers to a treatment regimen (or the portion of a treatment regimen) that is used for the maintenance of a patient during treatment of an illness, e.g., to keep the patient in remission for long periods of time (months or years) following the induction period. In some embodiments, the disclosed methods, uses and regimens employ a maintenance regimen. A maintenance regimen may employ continuous therapy (e.g., administering a drug at a regular intervals, e.g., weekly, monthly [every 4 weeks], yearly, etc.) or intermittent therapy (e.g., interrupted treatment, intermittent treatment, treatment at relapse, or treatment upon achievement of a particular predetermined criteria [e.g., pain, disease manifestation, PASI score, etc.]). Dose escalation may occur during a maintenance regimen.

Measures of GPP disease burden include the Body Surface area Affected (BSA), Japanese Dermatological Association (JDA) severity index for GPP, Clincal Global Impression (CGI) assessment, and/or Psoriasis Area and Severity Index (PAST). In some embodiments, the BSA, JDA, CGI and/or PASI assessments are employed to show improvement in GPP following treatment with the IL-17 antibody (e.g., secukinumab).

In the PASI scoring system, the head, trunk, upper limbs and lower limbs are assessed separately for erythema, thickening (plaque elevation, induration), and scaling (desquamation) as defined in Table 1. The average degree of severity of each sign in each of the four body regions is assigned a score of 0 to 4. The area covered by lesions on each body region is estimated as a percentage of the total area of that particular body region. Because the head and neck, upper limbs, trunk and lower limbs correspond to approximately 10%, 20%, 30% and 40% of the body surface area, respectively, the PASI score is calculated using the formula:

$$PASI=0.1(EH+IH+DH)AH+0.2(EU+IU+DU)AU+0.3(ET+IT+DT)AT+0.4(EL+IL+DL)AL$$

PASI scores can range from a lower value of 0, corresponding to no signs of psoriasis, up to a theoretic maximum of 72.0. PASI scores may be used to be specific to a tenth of a point, e.g., 9.0, 10.1, 14.2, 17.3, etc, or rounded to integer numbers. Further information on PASI scoring is available in Henseler T, Schmitt-Rau K (2008) Int. J. Dermatol.; 47: 1019-1023.

TABLE 1

The PASI Scoring System.

| Body Region | Erythema (E) | Thickening (I) (plaque levation, induration) | Scaling (D) (desquamation) | Area score (A) (based on true area %)* |
|---|---|---|---|---|
| Head and neck (H) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |
| Upper limbs (U) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |
| Trunk, axillae and groin (T) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |
| Lower limbs and buttocks (L) | 0 = none | 0 = none | 0 = none | 0 = 0% |
| | 1 = slight | 1 = slight | 1 = slight | 1 = 1-9% |
| | 2 = moderate | 2 = moderate | 2 = moderate | 2 = 10-29% |
| | 3 = severe | 3 = severe | 3 = severe | 3 = 30-49% |
| | 4 = very severe | 4 = very severe | 4 = very severe | 4 = 50-69% |
| | | | | 5 = 70-89% |
| | | | | 6 = 90-100% |

The following PASI definitions are used according to Committee for medicinal products for human use (CHMP), European Medicines Agency for the Evaluation of Medicines for Human Use. (2004) Guideline on clinical investigation of medicinal products indicated for the treatment of psoriasis. CHMP/EWP/2454/02 corr document. London, UK:

Treatment response (responder): Patients achieving ≥75% improvement (reduction) in Psoriasis Area and Severity Index (PAST) score compared to baseline (also referred to as PASI 75) are defined as treatment responders.

Partial response (partial responder): Patients achieving a ≥50% improvement from baseline PASI score (also referred to as PASI 50) but less than 75% (also referred to as PASI 75) are defined as partial responders.

Non response (non-responder): Patients achieving a PASI reduction of <50% from baseline PASI score are defined as non-responders.

Relapse (relapser): If patients loose ≥50% of the PASI gain achieved during the previous time in the study, patients will be regarded as having a "relapse".

Rebound (rebounder): Worsening of the value at baseline PASI (or new pustular, erythrodermic or more inflammatory psoriasis occurring within 8 weeks of stopping therapy), e.g., a PASI of >125% of the value at baseline PASI.

The JDA severity index rating scale for GPP is shown in Table 2:

TABLE 2

JDA Severeity Index for GPP (JDA severity Index for GPP; total score 0-17. Assessment of skin lesions: area of erythema with pustules, area of erythema, and area of edema; each score 0-3. Assessment of systemic manifestations and laboratory findings: fever, WBC count, CRP and serum albumin; each score 0-2).

| | Score | | | |
|---|---|---|---|---|
| | 0 | 1 | 2 | 3 |
| Assessment of skin lesions | | | | |
| Area of erythema with pustules* | 0% | >0%, <10% | ≥10%, <50% | ≥50% |
| Area of erythema (total)* | 0% | >0%, <25% | ≥25%, <75% | ≥75% |
| Area of edema* | 0% | >0%, <10% | ≥10%, <50% | ≥50% |
| Assessment of systemic manifestations and laboratory findings | | | | |
| Fever (° C.) | <37 | ≥37, <38.5 | ≥38.5 | — |
| WBC count (μl) | <10,000 | ≥10,000, <15,000 | ≥15,000 | — |
| CRP (mg/dl) | <0.3 | ≥0.3, <7 | ≥7 | — |
| Serum albumin (g/dl) | ≥3.8 | <3.8, ≥3 | <3 | — |

Severity index (severity score): 1-6 = mild; 7-10 = moderate; 11-17 = severe
*Percentage of overall body surface area The JDA severity index for GPP is derived as indicated in Table 2. Area of erythema with pustules, area of erythema (total), area of edema, fever, WBC, hsCRP and serum albumin are assessed separately. The total score of JDA severity index for GPP is assigned a score of 0-17. The percentage of affected overall body surface area is assessed for each symptom (erythema; erythema with pustules) using the palm method (where one palm of the subject equals 1% [one percent] of the overall body surface). The JDA severity index is a standardized and validated measurement for GPP in Japan (Iwatsuki et al. (2010), supra; Iwatsuki et al. (2010) Jpn. J. Dermatol. 120:815-839; see also Yamamoto et al. (2013) Disease Markers 34:153-161). In some embodiments, prior to treatment with the IL-17 antibody or antigen binding fragment thereof, the GPP patient has erythema area with pustule ≥10%.

The total Body Surface area Affected (BSA) by psoriasis is estimated from the percentages of areas affected by psoriasis, including head, trunk, upper limbs and lower limbs (see above for PASI assessment). Each reported percentage will be multiplied by its respective body region corresponding factor (head=0.1, trunk=0.3, upper limbs=0.2, lower limbs=0.4). The resulting four percentages will be added up to estimate the total BSA by psoriasis. In some embodiments, prior to treatment with the IL-17 antibody or antigen binding fragment thereof, the GPP patient has greater than at least 1% BSA by GPP, greater than at least 5% BSA by GPP, greater than at least 10% BSA by GPP, greater than at least 25% BSA by GPP, or greater than at least 50% BSA by GPP.

The Clinical Global Impression (CGI) assessment is conducted as indicated in Table 3. CGI is evaluated based on the change of the total score of JDA severity index for GPP at a given visit, relative to baseline (BSL).

TABLE 3

CGI assessment.

| | Change of total score of JDA severity index for GPP | and/or | Other reference |
|---|---|---|---|
| Very much improved | reduction by three points or more | or | Clear or almost clear of signs of GPP |
| Much improved | reduction by one or two points | or | At least one of the following: Erythema area with pustules (%) reduced by ≤30% compared to BSL* or Clinically meaningful improvement in at least two other components of the JDA severity index for GPP (erythema area, edema area, Fever, WBC, CRP, Alb) |
| Minimally improved | 0 points (No change) | and | At least one of the following: Erythema area with pustules (%) reduced by ≤20% compared to BSL* or Clinically meaningful improvement in at least one other component of the JDA severity index for GPP (erythema area, edema area, Fever, WBC, CRP, Alb) |
| No change | 0 points (No change) | and | Not meeting the other criteria of "minimally improved" |
| Worsened | ≥+1 point | — | Not applicable |

The phrase "means for administering" is used to indicate any available implement for systemically administering a drug to a patient, including, but not limited to, a pre-filled syringe, a vial and syringe, an injection pen, an autoinjector, an i.v. drip and bag, a pump, a patch pump, etc. With such items, a patient may self-administer the drug (i.e., administer the drug on their own behalf) or a physician may administer the drug. Typically, dosages given in "mg/kg" are administered via an i.v. route, and doses given in "mg" are administered via i.m. or s.c. injections. In some embodiments of the disclosed methods, kits, regimens and uses, the IL-17 antibody or antigen binding fragment thereof, e.g., secukinumab, is delivered to the patient via the i.v. route. In some embodiments of the disclosed methods, kits, regimens and uses, the IL-17 antibody or antigen binding fragment thereof, e.g., secukinumab, is delivered to the patient via the s.c. route.

"Generalized Pustular Psoriasis" and "GPP" refers to a variant of pustular psoriasis characterized by fever, chills, rigors and generalized pustule (histopahologically characterized by Kogoj's spongiform pustules) formation of the skin (Iizuka et al (2003) Arch Dermatol Res 295:S55-S59). GPP includes von Zumbusch (acute GPP), generalized form of acrodermatitis continua (Hallopeau), acute exanthematic GPP of pregnancy (impetigo herpetiformis), infantile and juvenile GPP, and circinate annular GPP (Farber and Nall, supra; Iizuka et al., supra). In some embodiments of the disclosed methods, kits, regimens and uses, the patient has von Zumbusch GPP, generalized form of acrodermatitis continua (Hallopeau), acute exanthematic, GPP of pregnancy (impetigo herpetiformis), infantile or juvenile GPP, or circinate annular GPP.

GPP can occur in patients with a history of ordinary psoriasis (psoriasis vulgaris) ("GPP with psoriasis vulgaris") and in patients without any history of ordinary psoriasis ("GPP without psoriasis vulgaris") (Iizuka et al. supra). In some embodiments of the disclosed methods, kits, regimens and uses, the patient has GPP with PV. In other embodiments, the patient has GPP without PV.

It has recently been determined that the majority of patients having GPP without PV have a deficiency of Interleukin-36 Receptor Antagonist protein found in their epidermis, resulting from homozygous or compound-heterozygous IL36RN mutations (Sugiura et al., supra). In some embodiments of the disclosure, the patient has a decreased level of Interleukin-36 Receptor Antagonist (e.g., mRNA or protein) in the skin relative to a subject not having GPP. In some embodiments of the disclosure, the patient is selected for treatment with the IL-17 antibody or antigen binding fragment thereof (e.g., secukinumab) based on having been previously determined to have a decreased level of Interleukin-36 Receptor Antagonist (mRNA or protein) in the skin relative to a subject not having GPP.

Yamamoto et al. (2013), supra have determined that IL-10 and IL-22 are significantly decreased in serum of GPP patients in parallel with their GPP score, making these two serum cytokines useful to evalue the efficacy of treatment for GPP. In some embodiments of the disclosed methods, kits, regimens and uses, a decrease in the level of IL-10 and/or level of IL-22 is used to assess improvement in GPP score in response to treatment with an IL-17 antibody or antigen binding fragment thereof (e.g., secukinumab).

IL-17 Antibodies and Antigen Binding Fragments Thereof

The various disclosed pharmaceutical compositions, regimens, processes, uses, methods and kits utilize an IL-17 antibody or antigen binding fragment thereof, e.g., secukinumab.

In one embodiment, the IL-17 antibody or antigen binding fragment thereof, e.g., secukinumab, comprises at least one immunoglobulin heavy chain variable domain ($V_H$) comprising hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3. In one embodiment, the IL-17 antibody or antigen binding fragment thereof, e.g., secukinumab, comprises at least one immunoglobulin light chain variable domain ($V_L$) comprising hypervariable regions CDR1', CDR2' and CDR3', said CDR1' having the amino acid sequence SEQ ID NO:4, said CDR2' having the amino acid sequence SEQ ID NO:5 and said CDR3' having the amino acid sequence SEQ ID NO:6. In one embodiment, the IL-17 antibody or antigen binding fragment thereof, e.g., secukinumab, comprises at least one immunoglobulin heavy chain variable domain ($V_H$) comprising hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13.

In one embodiment, the IL-17 antibody or antigen binding fragment thereof, e.g., secukinumab, comprises at least one immunoglobulin $V_H$ domain and at least one immunoglobulin $V_L$ domain, wherein: a) the immunoglobulin $V_H$ domain comprises (e.g., in sequence): i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the immunoglobulin $V_L$ domain comprises (e.g., in sequence) hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antibody or antigen binding fragment thereof, e.g., secukinumab, comprises: a) an immunoglobulin heavy chain variable domain ($V_H$) comprising the amino acid sequence set forth as SEQ ID NO:8; b) an immunoglobulin light chain variable domain ($V_L$) comprising the amino acid sequence set forth as SEQ ID NO:10; c) an immunoglobulin $V_H$ domain comprising the amino acid sequence set forth as SEQ ID NO:8 and an immunoglobulin $V_L$ domain comprising the amino acid sequence set forth as SEQ ID NO:10; d) an immunoglobulin $V_H$ domain comprising the hypervariable regions set forth as SEQ ID NO:1, SEQ ID NO:2, and SEQ ID NO:3; e) an immunoglobulin $V_L$ domain comprising the hypervariable regions set forth as SEQ ID NO:4, SEQ ID NO:5 and SEQ ID NO:6; f) an immunoglobulin $V_H$ domain comprising the hypervariable regions set forth as SEQ ID NO:11, SEQ ID NO:12 and SEQ ID NO:13; g) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; or h) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

For ease of reference the amino acid sequences of the hypervariable regions of the secukinumab monoclonal antibody, based on the Kabat definition and as determined by the X-ray analysis and using the approach of Chothia and coworkers, is provided in Table 4, below.

TABLE 4

Amino acid sequences of the hypervariable regions of the secukinumab monoclonal antibodies.

Light-Chain

| CDR1' | Kabat | R-A-S-Q-S-V-S-S-S-Y-L-A (SEQ ID NO: 4) |
|---|---|---|
|  | Chothia | R-A-S-Q-S-V-S-S-S-Y-L-A (SEQ ID NO: 4) |
| CDR2' | Kabat | G-A-S-S-R-A-T (SEQ ID NO: 5) |
|  | Chothia | G-A-S-S-R-A-T (SEQ ID NO: 5) |
| CDR2' | Kabat | Q-Q-Y-G-S-S-P-C-T (SEQ ID NO: 6) |
|  | Chothia | Q-Q-Y-G-S-S-P-C-T (SEQ ID NO: 6) |

Heavy-Chain

| CDR1 | Kabat | N-Y-W-M-N (SEQ ID NO: 1) |
|---|---|---|
| CDR1-x | Chothia | G-F-T-F-S-N-Y-W-M-N (SEQ ID NO: 11) |
| CDR2 | Kabat | A-I-N-Q-D-G-S-E-K-Y-Y-V-G-S-V-K-G (SEQ ID NO: 2) |
| CDR2-x | Chothia | A-I-N-Q-D-G-S-E-K-Y (SEQ ID NO: 12) |
| CDR3 | Kabat | D-Y-Y-D-I-L-T-D-Y-Y-I-H-Y-W-Y-F-D-L (SEQ ID NO: 3) |
| CDR3-x | Chothia | C-V-R-D-Y-Y-D-I-L-T-D-Y-Y-I-H-Y-W-Y-F-D-L-W-G (SEQ ID NO: 13) |

In preferred embodiments, the constant region domains preferably also comprise suitable human constant region domains, for instance as described in "Sequences of Proteins of Immunological Interest", Kabat E. A. et al, US Department of Health and Human Services, Public Health Service, National Institute of Health. The DNA encoding the VL of secukinumab is set forth in SEQ ID NO:9. The DNA encoding the VH of secukinumab is set forth in SEQ ID NO:7.

In some embodiments, the IL-17 antibody or antigen binding fragment thereof, e.g., secukinumab, comprises the three CDRs of SEQ ID NO:10. In other embodiments, the IL-17 antibody comprises the three CDRs of SEQ ID NO:8. In other embodiments, the IL-17 antibody comprises the three CDRs of SEQ ID NO:10 and the three CDRs of SEQ ID NO:8. CDRs of SEQ ID NO:8 and SEQ ID NO:10, according to both the Chothia and Kabat definition, may be found in Table 4.

In some embodiments, the IL-17 antibody or antigen binding fragment thereof, e.g., secukinumab, comprises the light chain of SEQ ID NO:15. In other embodiments, the IL-17 antibody or antigen binding fragment thereof, e.g., secukinumab, comprises the heavy chain of SEQ ID NO:17. In other embodiments, the IL-17 antibody or antigen binding fragment thereof, e.g., secukinumab, comprises the light chain of SEQ ID NO:15 and the heavy domain of SEQ ID NO:17. In some embodiments, the IL-17 antibody or antigen binding fragment thereof, e.g., secukinumab, comprises the three CDRs of SEQ ID NO:15. In other embodiments, the IL-17 antibody or antigen binding fragment thereof, e.g., secukinumab, comprises the three CDRs of SEQ ID NO:17. In other embodiments, the IL-17 antibody or antigen binding fragment thereof, e.g., secukinumab, comprises the three CDRs of SEQ ID NO:15 and the three CDRs of SEQ ID NO:17. CDRs of SEQ ID NO:15 and SEQ ID NO:17, according to both the Chothia and Kabat definition, may be found in Table 4. The DNA encoding the light chain of secukinumab is set forth as SEQ ID NO:14. The DNA encoding the heavy chain of secukinumab is set forth as SEQ ID NO:16.

Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g. of FR1 (amino acid 1 to 30 of SEQ ID NO:8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another preferred heavy chain framework consists in sequence of FR1-x (amino acid 1 to 25 of SEQ ID NO:8), FR2-x (amino acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO:10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, the IL-17 antibody or antigen binding fragment thereof, e.g., secukinumab, is selected from a human anti IL-17 antibody which comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof which comprises a variable domain comprising, in sequence, the hypervariable regions CDR1', CDR2', and CDR3' and the constant part or fragment thereof of a human light chain, said CDR1' having the amino acid sequence SEQ ID NO: 4, said CDR2' having the amino acid sequence SEQ ID NO:5, and said CDR3' having the amino acid sequence SEQ ID NO:6.

In one embodiment, the IL-17 antibody or antigen binding fragment thereof, e.g., secukinumab, is selected from a single chain binding molecule which comprises an antigen binding site comprising: a) a first domain comprising, in sequence, the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising, in sequence, the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, the IL-17 antibody or antigen binding fragment thereof, e.g., secukinumab, for use in the disclosed methods may comprise a derivative of the molecules set forth herein by sequence (e.g., a pegylated version of secukinumab). Alternatively, the $V_H$ or $V_L$ domain of the IL-17 antibody or antigen binding fragment thereof, e.g., secukinumab, for use in the disclosed methods may have $V_H$ or $V_L$ domains that are substantially identical to the $V_H$ or $V_L$ domains set forth herein (e.g., those set forth in SEQ ID NO:8 and 10). A human IL-17 antibody disclosed herein may comprise a heavy chain that is substantially identical to that set forth as SEQ ID NO:17 and/or a light chain that is substantially identical to that set forth as SEQ ID NO:15. A human IL-17 antibody disclosed herein may comprise a heavy chain that comprises SEQ ID NO:17 and a light chain that comprises SEQ ID NO:15. A human IL-17 antibody disclosed herein may comprise: a) one heavy chain which comprises a variable domain having an amino acid sequence substantially identical to that shown in SEQ ID NO:8 and the constant part of a human heavy chain; and b) one light chain which comprises a variable domain having an amino acid sequence substantially identical to that shown in SEQ ID NO:10 and the constant part of a human light chain. Alternatively, the IL-17 antibody or antigen binding fragment thereof, e.g., secukinumab, for use in the disclosed methods may be an amino acid sequence variant of the reference molecules set forth herein. In all such cases of derivative and variants, the IL-17 antibody or antigen binding fragment thereof, e.g., secukinumab, is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

The inhibition of the binding of IL-17 to its receptor may be conveniently tested in various assays including such assays as described in WO 2006/013107. By the term "to the same extent" is meant that the reference and the derivative molecules exhibit, on a statistical basis, essentially identical IL-17 inhibitory activity in one of the assays referred to herein (see Example 1 of WO 2006/013107). For example, the IL-17 antibody or antigen binding fragment thereof disclosed herein typically have $IC_{50}$s for the inhibition of human IL-17 on IL-6 production induced by human IL-17 in human dermal fibroblasts which are below about 10 nM, more preferably about 9, 8, 7, 6, 5, 4, 3, 2, or about 1 nM of that of, preferably substantially the same as, the $IC_{50}$ of the corresponding reference molecule when assayed as described in Example 1 of WO 2006/013107. Alternatively, the assay used may be an assay of competitive inhibition of binding of IL-17 by soluble IL-17 receptors (e.g. the human IL-17 R/Fc constructs of Example 1 of WO 2006/013107) and the IL-17 antibodies or antigen binding fragments thereof of the disclosure.

The disclosure also includes IL-17 antibodies or antigen binding fragments thereof, e.g., secukinumab, in which one or more of the amino acid residues of the $V_H$ or $V_L$ domain, typically only a few (e.g., 1-10), are changed relative to the $V_H$ or $V_L$ domain set forth as SEQ ID NO:8 and SEQ ID NO:10; for instance by mutation, e.g., site directed mutagenesis of the corresponding DNA sequences. The disclosure includes the DNA sequences coding for such changed IL-17 antibodies.

The disclosure also includes IL-17 antibodies or antigen binding fragments thereof, e.g., secukinumab, that have binding specificity for human IL-17, in particular IL-17 antibodies capable of inhibiting the binding of IL-17 to its receptor and IL-17 antibodies capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50% (said inhibitory activity being measured on IL-6 production induced by hu-IL-17 in human dermal fibroblasts).

In some embodiments, the IL-17 antibody, e.g., secukinumab, binds to an epitope of mature human IL-17 comprising Leu74, Tyr85, His86, Met87, Asn88, Val124, Thr125, Pro126, Ile127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain. The residue numbering scheme used to define these epitopes is based on residue one being the first amino acid of the mature protein (ie., IL-17A lacking the 23 amino acid N-terminal signal peptide and beginning with Glycine). The sequence for immature IL-17A is set forth in the Swiss-Prot entry Q16552. In some embodiments, the IL-17 antibody has a $K_D$ of about 100-200 pM, e.g., as measured by Biacore®. In some embodiments, the IL-17 antibody has an $IC_{50}$ of about 0.4 nM for in vitro neutralization of the biological activity of about 0.67 nM human IL-17A. In some embodiments, the absolute bioavailability of subcutaneously (s.c.) administered IL-17 antibody has a range of about 60-about 80%, e.g., about 76%. In some embodiments, the IL-17 antibody, such as secukinumab, has an elimination half-life of about 4 weeks (e.g., about 23 to about 35 days, about 23 to about 30 days, e.g., about 30 days). In some embodiments, the IL-17 antibody, such as secukinumab, has a $T_{max}$ of about 7-8 days.

Particularly preferred IL-17 antibodies or antigen binding fragments thereof, e.g., secukinumab, for use in the disclosed methods, uses, kits, etc. are human antibodies, especially secukinumab as described in Examples 1 and 2 of WO 2006/013107 (U.S. Pat. No. 7,807,155, which is incorporated by reference herein in its entirety). Secukinumab is a recombinant high-affinity, fully human monoclonal anti-human interleukin-17A (IL-17A, IL-17) antibody of the IgG1/kappa isotype that is currently in clinical trials for the treatment of immune-mediated inflammatory conditions. Secukinumab (see, e.g., WO2006/013107 and WO2007/117749) has a very high affinity for IL-17, i.e., a $K_D$ of about 100-200 pM (e.g., as measured by Biacore®) and an $IC_{50}$ for in vitro neutralization of the biological activity of about 0.67 nM human IL-17A of about 0.4 nM. Thus, secukinumab inhibits antigen at a molar ratio of about 1:1. This high binding affinity makes the secukinumab antibody particularly suitable for therapeutic applications. Furthermore, it has been determined that secukinumab has a very long half life, i.e., about 4 weeks, which allows for prolonged periods between administration, an exceptional property when treating chronic life-long disorders, such as psoriasis.

Other IL-17 antagonists (e.g., IL-17 antibodies, IL-17 receptor decoys, and IL-17 receptor antibodies) for use in the disclosed methods, kits and uses are those set forth in U.S. Pat. Nos. 8,057,794; 8,003,099; 8,110,191; and 7,838,638; International Patent Publication WO13011368 and US Published Patent Application Nos: 20120034656 and 20110027290.

Regimens, Methods of Treatment and Uses

Generalized Pustular Psoriasis (GPP)

It will be understood that IL-17 antibodies or antigen binding fragments thereof, e.g., secukinumab, are useful for the treatment, prevention, or amelioration of GPP.

The IL-17 antibodies or antigen binding fragments thereof, e.g., secukinumab, may be used in vitro, ex vivo, or incorporated into pharmaceutical compositions and administered to individuals (e.g., human patients) in vivo to treat, ameliorate, or prevent GPP. A pharmaceutical composition will be formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

The IL-17 antibodies or antigen binding fragments thereof, e.g., secukinumab, may be used as a pharmaceutical composition when combined with a pharmaceutically acceptable carrier. Such a composition may contain, in addition to an IL-17 antibodies or antigen binding fragments thereof, e.g., secukinumab, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the IL-17 binding molecules, or to minimize side effects caused by the IL-17 antibodies or antigen binding fragments thereof, e.g., secukinumab.

Pharmaceutical compositions for use in the disclosed methods may be manufactured in conventional manner. The use of antibodies as the active ingredient of pharmaceuticals is now widespread, including the products Herceptin® (trastuzumab), Rituxan® (rituximab), Synagis® (palivizumab), etc. Techniques for lyophilisation, preparation of aqueous formulations, and purification of antibodies to a pharmaceutical grade are well known in the art.

Antibodies, e.g., antibodies to IL-17, are typically formulated either in aqueous form ready for parenteral administration or as lyophilisates for reconstitution with a suitable diluent prior to administration. In some embodiments of the disclosed methods and uses, the IL-17 antibody, e.g., secukinumab, is formulated as a lyophilisate. Suitable lyophilisate formulations can be reconstituted in a small liquid volume (e.g., 2 ml or less) to allow subcutaneous administration and can provide solutions with low levels of antibody aggregation. For immediate administration it is dissolved in a suitable aqueous carrier, for example sterile water for injection or sterile buffered physiological saline. If it is considered desirable to make up a solution of larger volume for administration by infusion rather than a bolus injection, may be advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

In some embodiments of the disclosed methods and uses, the IL-17 antibody, e.g., secukinumab, is provided in aqueous forms for immediate use.

When a therapeutically effective amount of an IL-17 antibody or antigen binding fragment thereof, e.g., secukinumab, is administered by intravenous, cutaneous or subcutaneous injection, the IL-17 antibody will be in the form of a pyrogen-free, parenterally acceptable solution. A pharmaceutical composition for intravenous, cutaneous, or subcutaneous injection may contain, in addition to the IL-17 antibody or antigen binding fragments thereof, e.g., secukinumab, an isotonic vehicle such as sodium chloride, Ringer's, dextrose, dextrose and sodium chloride, lactated Ringer's, or other vehicle as known in the art.

The appropriate dosage will, of course, vary depending upon, for example, the particular IL-17 antibodies or antigen binding fragments thereof, e.g., secukinumab, to be employed, the host, the mode of administration and the nature and severity of the condition being treated, and on the nature of prior treatments that the patient has undergone. Ultimately, the attending health care provider will decide the amount of the IL-17 antibody with which to treat each individual patient. In some embodiments, the attending health care provider may administer low doses of the IL-17 antibody and observe the patient's response. In other embodiments, the initial dose(s) of IL-17 antibody administered to a patient are high, and then are titrated downward until signs of relapse occur. Larger doses of the IL-17 antibody may be administered until the optimal therapeutic effect is obtained for the patient, and the dosage is not generally increased further.

An IL-17 antibodies or antigen binding fragments thereof, e.g., secukinumab, is conveniently administered parenterally, intravenously, e.g., into the antecubital or other peripheral vein, intramuscularly, or subcutaneously. The duration of therapy using a pharmaceutical composition of the present disclosure will vary, depending on the severity of the disease being treated and the condition and personal response of each individual patient. The health care provider will decide on the appropriate duration of i.v. or s.c. therapy and the timing of administration of the therapy, using the pharmaceutical composition of the present disclosure.

The timing of dosing is generally measured from the day of the first dose of the active compound (e.g., secukinumab), which is also known as "baseline". However, different health care providers use different naming conventions, as shown in Table 5, below.

TABLE 5

Common naming conventions for dosing regimens.
Bolded items refer to the naming convention used herein.

| | Week | | | | | | | | | |
|---|---|---|---|---|---|---|---|---|---|---|
| | 0/1 | 1/2 | 2/3 | 3/4 | 4/5 | 5/6 | 6/7 | 7/8 | 8/9 | Etc. |
| 1st day | 0/1 | 7/8 | 14/15 | 21/22 | 28/29 | 35/36 | 42/43 | 49/50 | 56/57 | Etc. |

Notably, week zero may be referred to as week 1 by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the IL-17 antibodies or antigen binding fragments thereof, e.g., secukinumab, regardless of whether the physician refers to a particular week as "week 1" or "week 2". As an example of naming using the convention designated herein, five doses of secukinumab administered weekly may be provided during week 0 (e.g., on about day 1), during week 1 (e.g., on about day 8), during week 2 (e.g., on about day 15), during week 3 (e.g., on about day 22), and during week 4 (e.g., on about day 29). It will be understood that a dose need not be provided at an exact time point, e.g., a dose due approximately on day 29 could be provided, e.g., on day 24 to day 34, e.g., day 30, as long as it is provided in the appropriate week.

In some embodiments, the disclosed methods and uses employ an initial (sometimes called "induction") regimen that lasts 1, 2, 3, 4, 5, 6, 7, 8, 9, 10, 11, 12, 13, 14, 15, or 16 weeks. In some embodiments, the initial regimen is weeks 0, 1, 2, and 3. In other embodiments, the induction regimen is eight or twelve weeks, preferably twelve weeks. In some embodiments, the induction regimen employs a loading regimen. In some embodiments, the loading regimen comprises administering several (e.g., 1, 2, 3, 4, 5, 6, 7, preferably 4 or 5) doses of about 150 mg-300 mg, e.g., about four or five doses of 150 mg or 300 mg (preferably five doses of about 150 mg-about 300 mg) of the IL-7 antibody, e.g., secukinumab. In further embodiments, loading doses are delivered weekly, bi-weekly, every other week, or monthly [every 4 weeks], preferably weekly. In some embodiments, the disclosed methods, kits and uses employ 150 mg or 300 mg of the IL-17 antibody, e.g., secukinumab by subcutaneous injection, with initial dosing at weeks 0, 1, 2 and 3.

In some embodiments, two additional doses (e.g., 150 mg or 300 mg) of the IL-17 antibody, e.g., secukinumab, may be provided (e.g., during the induction regimen), e.g., during week 8 and 12. In other embodiments, three additional doses (e.g., 150 mg or 300 mg) of secukinumab may be provided (e.g., during the induction regimen), e.g., during week 8, 9 and 12; week 8, 10 and 12; or week 8, 11, and 12 (preferably week 8, 9 and 12).

It will be understood that in some embodiments, the disclosed methods, uses and kits may require up-titration of the IL-17 antibody (e.g., secukinumab) (e.g., from 150 mg to 300 mg) and/or addition of a further dose the IL-17 antibody (e.g., secukinumab) (e.g., an additional dose at week nine). For example, following treatment with several doses of the IL-17 antibody (e.g., secukinumab), a clinician may perform an evaluation, e.g., PASI, JDA, CGI (e.g., clinical components of a CGI evaluation) to determine if the patient is responding as desired to the treatment. This evaluation may be performed at any time during the induction regimen, e.g., the evaluation may be performed between administration of the dose during week 4 and week 8, or the evaluation may be performed between administration of the dose during week 8 and week 12. In preferred embodiments, the evaluation is performed between administration of the dose during week 4 and week 8. As a result of the evaluation, the clinician may, e.g., assign the patient to a treatment assessment based on the evaluation that is performed. In some embodiments, assignment to a treatment assessment "very much improved" or "much improved" as part of a CGI evaluation provides an indication that no up-titration of the IL-17 antibody (e.g., secukinumab) is required, and assignment to a treatment assessment "worse", "no change" or "minimally improved" as part of a CGI evaluation provides an indication that up-titration of the IL-17 antibody (e.g., secukinumab) is required. Following evaluation and assignment to a treatment assessment, the patient may be administered the same dose, e.g., about 150 mg, of the IL-17 antibody (e.g., secukinumab) for the remainder of the induction regimen (e.g., during week 8 and 12) if no up-titration is required, or the patient may be administered an increased dose, e.g., a double dose (e.g., about 300 mg), of the IL-17 antibody (e.g., secukinumab) for the remainder of the induction regimen (e.g., during weeks 8, 9 and 12). If uptitration occurs during the induction regimen, generally the uptitrated dose will also be used during the maintenance regimen.

As used herein, "clinical components of a CGI" refers to area of erythema with pustules, area of erythema, areas of edema and fever measured as part of a CGI evaluation; it excludes levels of WBC, CRP and serum albumin.

An initial (induction) regimen for delivery of an IL-17 antibodies or antigen binding fragments thereof, e.g., secukinumab, may be designed using PK information (see Table 6), rather than specific dosages. For the disclosed regimens and methods, an artisan may deliver an IL-17 antibody or antigen binding fragment thereof, e.g., secukinumab, during an induction regimen to provide a mean trough level of about 29.2 µg/mL (with a 30-40% inter-patient variation). Alternatively, an artisan may deliver an IL-17 antibody or antigen binding fragment thereof, e.g., secukinumab, during an induction regimen to provide a $C_{max}$ for a typical 90 kg patient of between about 52 µg/ml-about 104 µg/ml. In some embodiments, the IL-17 antibody, e.g., secukinumab, has a $T_{max}$ of about 7-8 days and an elimination half-life of about 30 days.

For a maintenance regimen, a dose may be provided every month (also called "monthly" dosing) (i.e., every 4 weeks, i.e., about every 28 days), every two months (i.e., every 8 weeks, i.e., about every 56 days), or every three months (i.e., every 12 weeks, i.e., about every 84 days). In some embodiments, the maintenance regimen begins following week 12. A first dose of a maintenance regimen will be administered on a date usually measured from the final dose of the induction regimen. Thus, as an example, if the final dose of the induction regimen is provided during week 12, then the first dose as part of a monthly [every 4 weeks] maintenance regimen will be delivered during week 16, the first dose as part of an every two month maintenance regimen will be delivered during week 20, the first dose as part of an every three month maintenance regimen will be delivered during week 24, etc. In some embodiments, the maintenance regimen comprises administering a dose of the IL-17 antibody or antigen binding fragment thereof, e.g., secukinumab, weekly, every two weeks, monthly [every 4 weeks], every other month, quarterly, bi yearly, or yearly. In some embodiments, the maintenance regimen employs monthly dosing (every 4 weeks). In some embodiments, the first dose of the maintenance regimen is delivered during week 4 or during 16. In some embodiments, the maintenance regimen comprises administering a dose of about 150 mg-300 mg, e.g., about 150 mg or about 300 mg of the IL-17 antibody or antigen binding fragment thereof, e.g., secukinumab. In some embodiments the patient is administered a dose of about 150 mg-about 300 mg (e.g., about 150 mg or about 300 mg) by subcutaneous injection with initial dosing at weeks 0, 1, 2 and 3, followed by monthly maintenance dosing, starting at week 4. A 300 mg dose may be given as two subcutaneous injections of 150 mg.

It will be understood that in some embodiments, a maintenance regimen may require up-titration (e.g., from 150 mg to 300 mg) and/or addition of further doses. For example, any time during the maintenance regimen, a clinician may perform an evaluation, e.g., PASI, JDA, CGI (e.g., clinical components of a CGI evaluation) to determine if the patient is responding as desired to the treatment. The clinician may thereafter assign the patient to a treatment assessment based on the evaluation that is performed. In some embodiments, assignment to a treatment assessment "very much improved" or "much improved" as part of a CGI evaluation provides an indication that no up-titration of the IL-17 antibody (e.g., secukinumab) is required, and assignment to a treatment assessment "worse", "no change" or "minimally improved" as part of a CGI evaluation provides an indication that up-titration of the IL-17 antibody (e.g., secukinumab) is required. Following evaluation and assignment to a treatment assessment, the patient may be administered the same dose, e.g., about 150 mg, of the IL-17 antibody (e.g., secukinumab) for the remainder of the maintenance regimen if no up-titration is required, or the patient may be administered an increased dose, e.g., about 300 mg, of the IL-17 antibody (e.g., secukinumab) for the remainder of the maintenance regimen. If uptitration occurs during the maintenance regimen, generally the patient will remain on the uptitrated dose during the maintenance regimen.

A maintenance regimen for delivery of an IL-17 antibody, such as secukinumab, may also be designed using PK information (see Table 6), rather than specific dosages. For the disclosed regimens and methods, an artisan may deliver an IL-17 antibody, such as secukinumab, during a maintenance regimen to provide an average steady-state trough level of about 15 µg/mL (with a 30-40% inter-patient variation). Alternatively, an artisan may deliver an IL-17 antibody, e.g., secukinumab, during an induction regimen to provide an average steady-state trough level for a typical 90 kg patient of between about 5 µg/ml-about 70 µg/ml, e.g., about 5 µg/ml-about 33 µg/ml or about 11 µg/ml-about 70 µg/ml, preferably about 16 µg/ml or about 33 µg/ml. In some embodiments, the IL-17 antibody, e.g., secukinumab, has a $T_{max}$ of about 7-8 days. In some embodiments, the IL-17 antibody, e.g., secukinumab, has an elimination half-life of about 30 days.

Delivery of an IL-17 antibody, such as secukinumab, during a loading regimen, induction regimen and/or maintenance regimen may be via a subcutaneous route, e.g., delivery of dosages of about 75 mg-about 300 mg (e.g., about 50 mg, about 75 mg, about 100 mg, about 125 mg, about 150 mg, about 175 mg, about 200 mg, about 225 mg, about 250 mag, about 275 mg, about 300 mg, about 325 mg), via an intravenous route, e.g., delivery of dosages of about 1 mg/kg-about 50 mg/kg (e.g., about 1 mg/kg, about 3 mg/kg, about 10 mg/kg, about 30 mg/kg, about 40 mg/kg, about 50 mg/kg, etc.) or any other route of administration (e.g, intramuscular, i.m.). In preferred embodiments, the dose of the IL-17 antibody is delivered s.c.

Disclosed herein are methods of treating Generalized Pustular Psoriasis (GPP), comprising administering to a patient in need thereof an IL-17 antibody or antigen binding fragment thereof, wherein the IL-17 antibody or antigen binding fragment binds to an epitope of an IL-17 homodimer having two mature human IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 antibody or antigen binding fragment thereof has a $K_D$ of about 100-about 200 pM (e.g., as measured by Biacore®), and wherein the IL-17 antibody or antigen binding fragment thereof has an in vivo half-life of about 23-about 30 days.

Disclosed herein are methods of treating GPP, comprising subcutaneously administering an IL-17 antibody or antigen binding fragment thereof to a patient in need thereof as a dose of about 150 mg-about 300 mg with initial dosing at weeks 0, 1, 2 and 3, followed by monthly dosing starting at week 4.

Disclosed herein are methods of treating GPP, comprising: a) subcutaneously administering an IL-17 antibody or antigen binding fragment thereof to a patient in need thereof at a dose of about 150 mg during weeks 0, 1, 2, 3, and 4; and b) thereafter, subcutaneously administering the IL-17 antibody or antigen binding fragment thereof to the patient at a dose of about 300 mg during week 8, 9, and 12 and then monthly thereafter, beginning during week 16.

Disclosed herein are methods of treating GPP, comprising: a) subcutaneously administering an IL-17 antibody or antigen binding fragment thereof to a patient in need thereof at a dose of about 150 mg during weeks 0, 1, 2, 3, and 4; b) assigning the patient to a treatment assessment based on clinical components of a CGI evaluation administered during week 8, wherein assigning a treatment assessment "very much improved" or "much improved" provides an indication that no up-titration is required, and wherein assigning a treatment assessment "worse", "no change" or "minimally improved" provides an indication that up-titration is required; and c) i) thereafter, subcutaneously administering the IL-17 antibody or antigen binding fragment thereof to the patient at a dose of about 150 mg monthly, beginning during week 8, if no up-titration is required; or ii) thereafter, subcutaneously administering the IL-17 antibody or antigen binding fragment thereof to the patient at a dose of about 300 mg during weeks 8, 9 and 12 and then monthly thereafter, beginning during week 16, if up-titration is required.

Disclosed herein are IL-17 antibodies or antigen binding fragments thereof for use in treating Generalized Pustular Psoriasis (GPP) in a patient in need thereof, characterized in that the IL-17 antibody or antigen binding fragment thereof binds to an epitope of an IL-17 homodimer having two mature human IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 antibody or antigen binding fragment thereof has a $K_D$ of about 100-about 200 pM (e.g., as measured by Biacore®), and wherein the IL-17 antibody or antigen binding fragment thereof has an in vivo half-life of about 23-about 30 days Disclosed herein are IL-17 antibodies or antigen binding fragments thereof for use in treating GPP in a patient in need thereof, characterized in that the IL-17 antibody or antigen binding fragment thereof is to be subcutaneously administered to the patient as a dose of about 150 mg-about 300 mg with initial dosing at weeks 0, 1, 2 and 3, followed by monthly dosing starting at week 4.

Disclosed herein are IL-17 antibodies or antigen binding fragments thereof for use in treating GPP in a patient in need thereof, characterized in that the IL-17 antibody or antigen binding fragment thereof is to be administered to the patient: a) subcutaneously at a dose of about 150 mg during weeks 0, 1, 2, 3, and 4; and b) thereafter, subcutaneously at a dose of about 300 mg during week 8, 9, and 12 and then monthly thereafter, beginning during week 16.

Disclosed herein are IL-17 antibodies or antigen binding fragments thereof for use in treating GPP in a patient in need thereof, characterized in that the IL-17 antibody or antigen binding fragment thereof is to be administered to the patient: a) subcutaneously at a dose of about 150 mg during weeks 0, 1, 2, 3, and 4; b) i) thereafter, subcutaneously at a dose of about 150 mg monthly, beginning during week 8, if no up-titration is required; or ii) thereafter, subcutaneously at a dose of about 300 mg during weeks 8, 9 and 12 and then monthly thereafter, beginning during week 16, if up-titration is required, wherein prior to step b), the patient is assigned to a treatment assessment based on clinical components of a CGI evaluation administered during week 8, wherein assigning a treatment assessment "very much improved" or "much improved" provides an indication that no up-titration is required, and wherein assigning a treatment assessment "worse", "no change" or "minimally improved" provides an indication that up-titration is required. In some embodiments of the disclosed methods or uses, the patient has von Zumbusch GPP, generalized form of acrodermatitis continua (Hallopeau), acute exanthematic, GPP of pregnancy (impetigo herpetiformis), infantile or juvenile GPP, or circinate or annular GPP.

In some embodiments of the disclosed methods or uses, the clinical components of the CGI are area of erythema with pustules, area of erythema, area of edema and fever.

In some embodiments of the disclosed methods or uses, the patient has a reduction in GPP as assessed by measuring levels of IL-10 and/or IL-22 in response to treatment with the IL-17 antibody.

In some embodiments of the disclosed methods or uses, the patient has a reduction in disease as assessed by the Japanese Dermatological Association (JDA) severity index for GPP, Clinical Global Impression (CGI) assessment, and/or Psoriasis Area and Severity Index (PAST) in response to treatment with the IL-17 antibody.

In some embodiments of the disclosed methods or uses, the patient has erythema with pustules ≥10% prior to treatment with the IL-17 antibody or antigen binding framente thereof (e.g., secukinumab). In some embodiments of the disclosed methods or uses, the patient has a Body Surface area Affected (BSA) of at least 5% or greater prior to treatment with the IL-17 antibody or antigen binding framente thereof (e.g., secukinumab). In some embodiments of the disclosed methods or uses, the patient has a Body Surface area Affected (BSA) of at least 10% or greater prior to treatment with the IL-17 antibody or antigen binding framente thereof (e.g., secukinumab).

In some embodiments of the disclosed methods or uses, the patient is able to stop or reduce concomitant use of a psoriasis agent by at least about 50% in response to treatment with the IL-17 antibody or antigen binding framente thereof (e.g., secukinumab). In some embodiments, the disclosed methods or uses, further comprise administering the patient at least one additional psoriasis agent. In some embodiments of the disclosed methods or uses, the additional psoriasis agent is selected from the group consisting of ustekinumab, a TNF alpha antagonist (such as etanercept, adalimumab, infliximab), a systemic corticosteroid, cyclosporin, etretinate, and methotrexate.

In some embodiments of the disclosed methods or uses, the patient has GPP without psoriasis vulgaris (PV). In some embodiments of the disclosed methods or uses, the patient has GPP with psoriasis vulgaris (PV). In some embodiments, the patient has a decreased level of Interleukin-36 Receptor Antagonist (e.g., mRNA or protein) in the skin relative to a subject not having GPP. In some embodiments, the patient is selected for treatment with the IL-17 antibody or antigen binding fragment thereof based on having been previously determined to have a decreased level of Interleukin-36 Receptor Antagonist (mRNA or protein) in the skin relative to a subject not having GPP.

As used herein, the phrase "container having a sufficient amount of the IL-17 antibody to allow delivery of [a designated dose]" is used to mean that a given container (e.g., vial, pen, syringe) has disposed therein a volume of an IL-17 antibody (e.g., as part of a pharmaceutical composition) that can be used to provide a desired dose. As an example, if a desired dose is 500 mg, then a clinician may use 2 ml from a container that contains an IL-17 antibody formulation with a concentration of 250 mg/ml, 1 ml from a container that contains an IL-17 antibody formulation with a concentration of 500 mg/ml, 0.5 ml from a container contains an IL-17 antibody formulation with a concentration of 1000 mg/ml, etc. In each such case, these containers have a sufficient amount of the IL-17 antibody to allow delivery of the desired 500 mg dose.

As used herein, the phrase "formulated at a dosage to allow [route of administration] delivery of [a designated dose]" is used to mean that a given pharmaceutical composition can be used to provide a desired dose of an IL-17 antibody, e.g., secukinumab, via a designated route of administration (e.g., s.c. or i.v.). As an example, if a desired subcutaneous dose is 500 mg, then a clinician may use 2 ml of an IL-17 antibody formulation having a concentration of 250 mg/ml, 1 ml of an IL-17 antibody formulation having a concentration of 500 mg/ml, 0.5 ml of an IL-17 antibody formulation having a concentration of 1000 mg/ml, etc. In each such case, these IL-17 antibody formulations are at a concentration high enough to allow subcutaneous delivery of the IL-17 antibody. Subcutaneous delivery typically requires delivery of volumes of less than about 2 ml, preferably a volume of about 1 ml or less. However, higher volumes may be delivered over time using, e.g, a patch/pump mechanism.

Disclosed herein is the use of an IL-17 antibody (e.g., secukinumab) for the manufacture of a medicament for the treatment of GPP in a patient, wherein the medicament is formulated to comprise containers, each container having a sufficient amount of the IL-17 antibody to allow delivery of at least about 75 mg, 150 mg or 300 mg IL-17 antibody or antigen binding framente thereof (e.g., secukinumab) per unit dose.

Disclosed herein is the use of an IL-17 antibody (e.g., secukinumab) for the manufacture of a medicament for the treatment of GPP in a patient, wherein the medicament is formulated at a dosage to allow systemic delivery (e.g., i.v. or s.c. delivery) 75 mg, 150 mg or 300 mg IL-17 antibody or antigen binding framente thereof (e.g., secukinumab) per unit dose.

Treat to Target (Plaque-Type Psoriasis)

This disclosure also contemplates improved treatment regimens for plaque-type psoriasis. Up-titration, optionally along with delivery of additional doses (e.g., 1 or 2 additional doses), can be employed to enhance treatment response in plaque-type psoriasis. According to International Patent Publication WO2012/045848, a plaque-type psoriasis patient is typically administered about 150 mg-about 300 mg secukinumab as part of an induction regimen at weeks 0, 1, 2, 3, 4, 5, 8, and 12 and thereafter the patient is typically administered about 150 mg-about 300 mg secukinumab as part of a monthly (i.e., every 4 weeks) maintenance regimen (i.e., on the whole, secukinumab is delivered weekly for four weeks, and every four weeks thereafter (starting at week 4)). An improved treatment regimen for plaque-type psoriasis includes treatment of the patient with about 150 mg secukinumab during week 0, 1, 2, 3, 4, and 8. However, prior to treatment at week 12, the patients's PASI score may be assessed and those patients not having achieved, e.g., PASI 75 or PASI 90 (preferably not having achieved PASI 90) at week 12 may be up-titrated to, e.g., a double dose (e.g., about 300 mg) of the IL-17 antibody (e.g., secukinumab) for a week 12 dose and, optionally, may be given an additional dose (e.g., a double dose (e.g., about 300 mg)) during week 13. These patients will be treated with the increased dose (e.g., the double dose (e.g., about 300 mg)) of the IL-17 antibody (e.g., secukinumab) during week 16 and monthly (i.e., every 4 weeks) thereafter. PASI 90 refers to ≥90% improvement (reduction) in PASI score compared to baseline.

Disclosed herein are methods of treating plaque-type psoriasis, comprising: a) administering an IL-17 antibody (e.g., secukinumab) to a patient in need thereof as weekly doses of about 150 mg during week 0, 1, 2, 3, 4, and 8; b) thereafter, determining whether the patient has achieved PASI 75 or PASI 90 (preferably PASI 90) before week 12; c) administering the patient about 300 mg of the IL-17 antibody during week 12 and, optionally seek 13, if the patient has not achieved PASI 75 or PASI 90 (preferably PASI 90) according to step b); and d) thereafter administering the IL-17 antibody to the patient monthly (i.e., every 4 week) at a dose of about 300 mg, beginning during week 16.

Another improved treatment regimen employing up-titration for plaque-type psoriasis includes treatment of the patient with about 150 mg secukinumab during week 0, 1, 2, 3, 4, 8 and 12. However, prior to treatment at week 16, the patients's PASI score may be assessed and those patients not having achieved, e.g., PASI 75 or PASI 90 (preferably not having achieved PASI 90) before week 16 may be up-titrated to, e.g., a double dose (e.g., about 300 mg) of the IL-17 antibody (e.g., secukinumab) for a week 16 dose. These patients will be treated with the increased dose (e.g., the double dose (e.g., about 300 mg)) of the IL-17 antibody (e.g., secukinumab) during Week 16 and monthly (i.e., every 4 weeks) thereafter.

Disclosed herein are methods of treating plaque-type psoriasis, comprising: a) administering an IL-17 antibody (e.g., secukinumab) to a patient in need thereof as weekly doses of about 150 mg during week 0, 1, 2, 3, 4, 8, and 12; b) thereafter, determining whether the patient has achieved PASI 75 or PASI 90 (preferably PASI 90) before week 16; and c) thereafter, administering the IL-17 antibody to the patient monthly (i.e., every 4 week) at a dose of about 300 mg, beginning during week 16, if the patient has not achieved PASI 75 or PASI 90 (preferably PASI 90) according to step b).

Another improved treatment regimen for plaque-type psoriasis includes down-titration of the amount of secukinumab given to the patient. In this manner, less antibody drug may be delivered to the patient, which is regarded as a safety benefit. For example, an improved treatment regimen for plaque-type psoriasis includes treatment of the patient with about 300 mg secukinumab during week 0, 1, 2, 3, 4, 8, and 12. However, prior to treatment at week 16, the patients's PASI score may be assessed and those patients having achieved, e.g., PASI 75 or PASI 90 (preferably having achieved PASI 90) before week 16 may be down-titrated to, e.g., about 150 mg of the IL-17 antibody (e.g., secukinumab), for a week 16 dose. These patients will be treated with this decreased dose (e.g., about 150 mg) of the IL-17 antibody (e.g., secukinumab) during week 16 and monthly (i.e., every 4 weeks) thereafter.

Disclosed herein are methods of treating plaque-type psoriasis, comprising: a) administering an IL-17 antibody (e.g., secukinumab) to a patient in need thereof as weekly doses of about 300 mg during week 0, 1, 2, 3, 4, 8, and 12; and b) thereafter, administering the IL-17 antibody to the patient monthly (i.e., every 4 week) at a dose of about 150 mg, beginning during Week 16.

Disclosed herein are methods of treating plaque-type psoriasis, comprising: a) administering an IL-17 antibody (e.g., secukinumab) to a patient in need thereof as weekly doses of about 300 mg during week 0, 1, 2, 3, 4, 8, and 12; b) thereafter, determining whether the patient has achieved PASI 75 or PASI 90 (preferably PASI 90) before week 16; and c) thereafter, administering the IL-17 antibody to the patient monthly (i.e., every 4 week) at a dose of about 150 mg, beginning during week 16, if the patient has achieved PASI 75 or PASI 90 (preferably PASI 90) according to step b).

Alternatively, improved treatment regimen for plaque-type psoriasis includes modification of the treatment timing (increased or decreased frequency of drug administration), rather than modification of the dosage (up-titration or down-titration of drug). Fore example, in one embodiment the patient is treated with about 150 mg or 300 mg (preferably about 150 mg) secukinumab during week 0, 1, 2, 3, 4, 8, and 12. However, prior to treatment (e.g., at week 16), the patients's PASI score may be assessed and if the patient has achieved clear or almost clear skin (e.g., PASI 90), the patient may thereafter be dosed less frequently during the maintenance regimen, e.g., every 6 weeks (rather than monthly [every 4 weeks]). If clearance (e.g., PASI90) is later lost, then these patients may resume treatment during the maintenance regimen on a monthly basis [every 4 weeks]. Conversely, those patients not having achieved clearance (e.g., PASI90) (e.g., before week 16) may be dosed more frequently during the maintenance regimen, e.g., every 2 weeks (rather than monthly [every 4 weeks]). If PASI90 is later achieved, then these patients may resume treatment during the maintenance regimen on a monthly basis [every 4 weeks]. Testing for PASI90 response with the goal to modify treatment timing may take place before treatment at week 8, 12, 16, 20, 24, etc. (preferably before week 16, most preferably between week 12 and 16).

Disclosed herein are methods of treating plaque-type psoriasis, comprising: a) administering an IL-17 antibody (e.g., secukinumab) to a patient in need thereof as weekly doses of about 150 mg to about 300 mg during week 0, 1, 2, 3, 4, 8, 12, 16, and 20; and b) thereafter, administering the patient about 150 mg to about 300 mg of the IL-17 antibody every 6 weeks, beginning during week 24.

Disclosed herein are methods of treating plaque-type psoriasis, comprising: a) administering an IL-17 antibody (e.g., secukinumab) to a patient in need thereof as weekly doses of about 150 mg to about 300 mg during week 0, 1, 2, 3, 4, 8, 12, 16, and 20; b) thereafter, determining whether the patient has achieved PASI 75 or PASI 90 (preferably PASI 90) by week 24; c) thereafter, administering the patient about 150 mg to about 300 mg of the IL-17 antibody every 6 weeks, beginning during week 24, if the patient has achieved PASI 75 or PASI 90 (preferably PASI 90) by week 24 according to step b).

Disclosed herein are methods of treating plaque-type psoriasis, comprising: a) administering an IL-17 antibody (e.g., secukinumab) to a patient in need thereof as weekly doses of about 150 mg to about 300 mg (e.g., about 150 mg or about 300 mg) during week 0, 1, 2, 3, 4, 8, and 12; and b) thereafter, administering the patient about 150 mg to about 300 mg (e.g., about 150 mg or about 300 mg) of the IL-17 antibody every 6 weeks, beginning during week 16.

Disclosed herein are methods of treating plaque-type psoriasis, comprising: a) administering an IL-17 antibody (e.g., secukinumab) to a patient in need thereof as weekly doses of about 150 mg to about 300 mg during week 0, 1, 2, 3, 4, 8, and 12; b) thereafter, determining whether the patient has achieved PASI 75 or PASI 90 (preferably PASI 90) by week 16; c) thereafter, administering the patient about 150 mg to about 300 mg of the IL-17 antibody every 6 weeks, beginning during week 16, if the patient has achieved PASI 75 or PASI 90 (preferably PASI 90) by week 16 according to step b).

Disclosed herein are methods of treating plaque-type psoriasis, comprising: a) administering an IL-17 antibody (e.g., secukinumab) to a patient in need thereof as weekly doses of about 150 mg to about 300 mg during week 0, 1, 2, 3, 4, 8, 12, 16, and 20; b) thereafter, determining whether the patient has achieved PASI 75 or PASI 90 (preferably PASI 90) by Week 24; c) thereafter, administering the patient about 150 mg to about 300 mg of the IL-17 antibody every 2 weeks, beginning during week 24, if the patient has not achieved PASI 75 or PASI 90 (preferably PASI 90) by week 24 according to step b).

Disclosed herein are methods of treating plaque-type psoriasis, comprising: a) administering an IL-17 antibody (e.g., secukinumab) to a patient in need thereof as weekly doses of about 150 mg to about 300 mg during week 0, 1, 2, 3, 4, 8, and 12; b) thereafter, determining whether the patient has achieved PASI 75 or PASI 90 (preferably PASI 90) by week 16; c) thereafter, administering the patient about 150 mg to about 300 mg of the IL-17 antibody every 2 weeks, beginning during week 16, if the patient has not achieved PASI 75 or PASI 90 (preferably PASI 90) by week 16 according to step b).

In some embodiments of the above methods, a physician may wish to employ less frequent maintenance dosing if the patient has maintained PASI90 for a given time (e.g., the patient displays PASI90 at week 8 through 12 [or at both week 8 and 12], at week 16 through week 24 [or at both week 16 and week 24]) or the patient has achieved PASI90 by a given time point (e.g., the patient displays PASI90 by week 8, by week 12, by week 16, etc.). In some embodiments of the above methods, the patient has not previously been treated with a biological molecule (e.g., a TNF alfa inhibitor, e.g., Enbrel®) for plaque-type psoriasis. In some embodiments of the above methods, the patient has achieved clear or almost clear skin (e.g., PASI 90) before q6w treatment begins. In some embodiments of the above methods, the patient has achieved clear or almost clear skin (e.g., PASI 90) before down-titration from 300 mg to 150 mg begins. In some embodiments of the above methods, the patient has moderate to severe plaque psoriasis. In some embodiments of the above methods, the patient has failed to respond to, or has a contraindication to, or is intolerant to phototherapy or systematic therapy, including ciclosporin or methotrexate (MTX).

Palmoplantar Pustular Psoriasis (PPP)

This disclosure also contemplates treatment regimens for pustular psoriasis that is confined to the palms and soles of a patient (palmoplantar pustular psoriasis, PPP). Around 20% of patients with PPP may develop plaque psoriasis symptoms elsewhere on their body. Most patients suffering from GPP will also present pustular symptoms on the palms and soles. Prevalence and incidence worldwide is low (e.g., 1.76/million in France), with the highest prevalence in Japan (7.46/million) (Augey (2006) Eur J Dermatol 16(6): 669-673). The prevalence of PPP is difficult to estimate, but some publications mention a prevalence of 0.01% in the general population (de Waal (2011) J Dermatolog Treat 22(2): 102-105).

High levels of IL-17A are found in tissue and fluids of patients suffering from PPP, and there is an up-regulation of IL-17 dependent genes in PPP (Yilmaz, supra; Bissonnette (2013) Journal of the American Academy of Dermatology 71st Annual Meeting of the American Academy of Dermatology, Miami Beach, Fla., US; Mar. 1-Mar. 5, 2013; Conference Publication: (var. pagings). 68 (4 SUPPL. 1) (pp. AB201). PPP is characterized by sterile pustules on the palms and soles, which erupt repeatedly over the months or years. The surrounding skin has a scaly and erythematous aspect with cracks that are often painful (Pettey (2003) Am Acad Dermatol 49(2): 271-275; de Waal, supra). The eruptions involve both hands and feet usually, sometimes limited to only hands or only feet. The skin lesions of palmoplantar pustular psoriasis exist for many years and are very resistant to treatment. Sometimes they disappear on their own, only to reappear again.

A variety of PPP treatments have been tried, including UV-therapy, but more severe cases or treatment resistant cases may require systemic treatment with methotrexate, cyclosporine, acitretin alone or in combination with cyclosporine, and biological agents. Acitrecin is the only product which has been approved in Europe for use in PPP. Among biological agents, the IL-12/23 inhibitor ustekinumab has been tried, but results are ambiguous. In a case series of four patients, two failed to improve (Gerdes (2010) Br J Dermatol 163(5): 1116-1118). Some authors (Bissonnett, supra) were not able to show clinical benefit with licensed doses of ustekinumab, while others recently presented a series of 5 case reports successfully treated with ustekinumab (Morales-Munera (2013) Br J Dermatol 168 (4): 820-824). A small placebo-controlled pilot study (n=15) with etanercept 50 mg twice weekly showed a statistically significant difference in ppPASI response at 24 weeks. At 12 weeks etanercept was numerically, but not statistically significantly better than placebo (Bissonnette, supra). Alefacept has been reported to be moderately effective in palmoplantar pustular psoriasis with reductions in palmoplantar pustulosis PASI (ppPASI) of 49.6% after 16 weeks of treatment (Guenther (2007) J Cutan Med Surg 11(6): 202-205). As a result of the difficulty in treating PPP and the ambiguous responses to currently available drugs, new treatments for PPP are needed.

IL-17 antibodies, such as secukinumab, are expected to find use in the treatment of PPP. A PPP patient is typically administered about 150 mg-about 300 mg of the IL-17 antibody (e.g., secukinumab) during weeks 0, 1, 2, and 3, and then monthly thereafter, beginning during week 4 (i.e., on the whole, secukinumab is delivered during week 0, 1, 2, 3, 4, 8, 12, 16, 20, 24, etc.). Clinical trial Protocol AIN457A3301, which is incorporated by reference herein, describes the protocol for this treatment regimen of PPP in detail. The study population comprises a representative group of male and female out-patients (18 years old) with moderate to severe palmoplantar pustular psoriasis (pp-PASI≥12 and DLQI≥10) that is poorly controlled by topical treatments and/or ultraviolet (UV) light and/or previous systemic therapy, and who are candidates for biological therapy.

Response to treatment for PPP patients may be measured by ppPASI. The ppPASI is a modification of the PASI score and adjusted for palmoplantar pustular psoriasis whereby the classification of thickening of the skin has been replaced by classification and scoring of vesicles/pustules (Fredriksson (1978) Dermatologica 157(4): 238-244). The maximum total score on the ppPASI system is 72. Other response indicies include: the PASI scoring system, Investigator's Global Assessment mod 2011 (IGA mod 2011), Dermatology Life Quality Index (DLQI) and Subject's Global Assessment (SGA), Work Productivity and Activity Impairment Questionnaire-Psoriasis (WPAI-PSO), Palmar-Pustular Quality of Life Index (ppQoL-Index).

Disclosed herein are methods of treating palmoplantar pustular psoriasis, PPP, comprising: subcutaneously administering an IL-17 antibody (e.g., secukinumab) to a patient in need thereof as a dose of about 150 mg to about 300 mg with initial dosing at weeks 0, 1, 2 and 3, followed by monthly maintenance dosing starting at week 4. In some embodiments, the patient has PPP accompanying chronic plaque-type psoriasis. In some embodiments, the patient has PPP accompanying GPP.

Combination Therapies

In practicing some of the methods of treatment or uses of the present disclosure, a therapeutically effective amount of an IL-17 antibody or antigen binding fragment thereof, e.g., secukinumab, is administered to a patient, e.g., a mammal (e.g., a human). While it is understood that the disclosed methods provide for treatment of patients with an IL-17 antibody, this does not imply that the IL-17 antibody-based therapy is necessarily a monotherapy. Indeed, if a patient is selected for treatment with an IL-17 antibody, then the IL-17 antibody (e.g., secukinumab) may be administered in accordance with the method of the disclosure either alone or in combination with other therapeutics for treating GPP, plaque-type psoriasis and/or PPP (as the case may be) disease in patients, e.g., in combination with cyclosporin. When coadministered with one or more additional therapeutics, an IL-17 antibody may be administered either simultaneously with the other therapeutic, or sequentially. If administered sequentially, the attending physician will decide on the appropriate sequence of administering the IL-17 antibody in combination with other therapeutics, as well as the appropriate dosages for co-delivery.

Various therapies may be beneficially combined with the disclosed IL-17 antibodies, such as secukinumab, during treatment of PV, GPP and/or PPP. Such therapies include topicals (over the counter, non-steroidal compounds and steroidal compound), phototherapy and systemic treatment (e.g., with biologis or chemical entities).

Non-limiting examples of topical psoriasis agents for use with the disclosed IL-17 antibodies, such as secukinumab, include salicylic acid, coal tar, Dovonex® (calcipotriene), Taclonex® (calcipotriene and betamethasone dipropionate), Tazorec® (tazarotene), pimecrolimus, tacrolimus, Vectical® (calcitriol), Zithranol-RR® (anthralin) and topical steroids (e.g., corticosteroids).

Examples of phototherapy for use with the disclosed IL-17 antibodies, such as secukinumab, include treatment with psoralen+UVA (PUVA) or treatment with UVB (with or without tar).

Examples of psoriasis agents used in systemic treatment for use with the disclosed IL-17 antibodies, such as secukinumab, include retionoids such as Acitretin (e.g., Soriatane®), cyclosporine, methotrexate, hydroxyurea (e.g., Hydrea®), isotretinoin, mycophenolate mofetil, mycophenolic acid, sulfasalazine, 6-thioguanine, fumarates (e.g, dimethylfumarate and fumaric acid esters), azathioprine, corticosteroids, leflunomide, tacrolimus, T-cell blockers (such as Amevive® (alefacept) and Raptiva® (efalizumab), tumor necrosis factor-alpha (TNF-alpha) blockers (such as Enbrel® (etanercept), Humira® (adalimumab), Remicade® (infliximab) and Simponi® (golimumab)) and interleukin 12/23 blockers (such as Stelara® (ustekinumab), tasocitinib, and briakinumab.

Additional psoriasis agents for use in combination with the disclosed IL-17 antibodies, such as secukinumab, during treatment of psoriasis include apremilast, mometasone, voclosporin, ketokonazol, Neuroskin Forte, recombinant human interleukin-10, voclosporin, MK-3222, tofacitinib, VX-765, MED-I545, fluphenazine decanoate, acetomuinophn, bimosiamose cream, doxycycline, vancomycin, AbGn168, Vitamin D3, R05310074, fludarabine Calcipotriol and hydrocortisone (LEO 80190), LE80185 (Taclonex® Scalp topical suspension/Xamiol® gel), Focetria (Monovalent MF59-Adjuvanted vaccine, tgAAC94 gene therapy vector, Apremilast, Capsaicin, Psirelax, ABT-874 (anti IL-12), IDEC-114, MEDI-522, INCB018424 phosphate cream, LE29102, BMS 587101, CD 2027, CRx-191, 8-methoxypsoralen or 5-methoxypsoralen, Bicillin L-A, LY2525623, INCB018424, LY2439821, CEP-701, CC-10004, certolizumab (CZP), GW786034 (pazopanib), doxycycline Curcuminoids C3 Complex, NYC 0462, RG3421, hOKT3gammal(Ala-Ala), BT061, teplizumab, Chondroitin sulphate, CNTO 1275, monoclonal antibody to IL-12p40 and IL-23 p40 subunits, BMS-582949, MK0873, MEDI-507, M518101, ABT-874, AMG 827, AN2728, AMG 714, AMG 139, PTH (1-34), U0267 Foam, CNTO 1275, QRX-101, CNTO 1959, LEO 22811, Imiquimod, CTLA4Ig, Alga Dunaliella Bardawil, AS101 Cream, pioglitazone, pimecrolimus, ranibizumab, Zidovudine CDP870 (Certolizumab pegol), Onercept (r-hTBP-1), ACT-128800, 4,4-dimethyl-benziso-2H-selenazine, CRx-191, CRx-197, doxercalciferol, LEO 19123 Cream (calcipotriol plus LEO 80122), LAS 41004, WBI-1001, tacrolimus, RAD001, rapamycin, rosiglitazone, pioglitazone, ABT-874, Aminopterin, AN2728, CD2027, ACT-128800, mometasone furoate, CT 327, clobetasol+LCD, BTT1023, E6201, topical vitamin B12, INCB018424 Phosphate Cream, Xamiol gel, IP10.C8, BFH772, LEO 22811, Fluphenazine, MM-093, Clobex, SCH 527123, CF101, SRT2104, BIRT2584, CC10004, Tetrathiomolybdate, CP-690,550, U0267, ASP015K, VB-201, Acitretin (also called U0279), RWJ-445380, Psoralait, Clobetasol propionate, botulinum toxin type A, alefacept, erlotinib, BCT194, Ultravate Ointment, Roflumilast, CNTO 1275, halobetasol, ILV-094, CTA018 cream, COL-121, MEDI-507, AEB071. Additional agents for use in combination with secukinumab during treatment of psoriasis include IL-6 antagonists, CD20 antagonistis, CTLA4 antagnonists, IL-17 antagonists, IL-8 antagnoists, IL-21 antagonistis, IL-22 antagonist, VGEF antagnosits, CXCL antagonists, MMP antagonists, defensin antagonists, IL-1beta antagonists, and IL-23 antagonists (e.g., receptor decoys, antagonistic antibodies, etc.). A skilled artisan will be able to discern the appropriate dosages of the above agents for co-delivery with the disclosed IL-17 antibodies, such as secukinumab.

In some embodiments of the disclosure, prior to treatment with the IL-17 antagonist, e.g., IL-17 antibodies or antigen binding fragments thereof, the patient is undergoing treatment with another psoriasis agent. In some embodiments of the disclosed methods, uses and kits, the additional psoriasis agent is selected from the group consisting of ustekinumab, a TNF alpha antagonist (such as etanercept, adalimumab, infliximab), a systemic corticosteroid, cyclosporin, etretinate, and methotrexate. In some embodiments of the disclosure, administration of the IL-17 antibody (e.g., secukinumab) allows the patient to completely stop the prior psoriasis treatment, or, in some embodiments, reduce concomittant use of the psoriasis agent by at least about 10%, about 20%, about 25%, about 50%, about 75%.

In further embodiments, the patient has not previously been treated for psoriasis (treatment naïve), has not previously been treated systemically for psoriasis (systemic treatment naïve) or has not previously been treated for psoriasis using a biological agent (biological naïve).

Kits

The disclosure also encompasses kits for treating a GPP, PPP or plaque-type psoriasis patient (as the case may be) with an IL-17 antibody or antigen binding fragment thereof, e.g., secukinumab. Such kits comprise an IL-17 antibody or antigen binding fragment thereof, e.g., secukinumab (e.g., in liquid or lyophilized form) or a pharmaceutical composition comprising the IL-17 antibody (described supra). Additionally, such kits may comprise means for administering the IL-17 antibody (e.g., a syringe and vial, a prefilled syringe, a prefilled pen, a patch/pump) and instructions for use. The instructions may disclose providing the IL-17 antibody (e.g., secukinumab) to the patient as part of a specific dosing regimen. These kits may also contain additional psoriasis agents (described supra) for treating psoriasis, e.g., for delivery in combination with the enclosed IL-17 antibody, e.g., secukinumab.

The phrase "means for administering" is used to indicate any available implement for systemically administering a drug top a patient, including, but not limited to, a pre-filled syringe, a vial and syringe, an injection pen, an autoinjector, an i.v. drip and bag, a pump, patch/pump, etc. With such items, a patient may self-administer the drug (i.e., administer the drug on their own behalf) or a care-giver or a physician may administer the drug.

Disclosed herein are kits for the treatment of a patient having GPP, comprising: a) a pharmaceutical composition comprising a therapeutically effective amount of an IL-17 antibody or antigen binding fragment thereof; b) means for administering the IL-17 antibody or antigen binding fragment thereof to the patient; and c) instructions providing subcutaneously administering an IL-17 antibody or antigen binding fragment thereof to a patient in need thereof as a dose of about 150 mg-about 300 mg with initial dosing at weeks 0, 1, 2 and 3, followed by monthly dosing starting at week 4.

Disclosed herein are kits for the treatment of a patient having GPP, comprising: a) a pharmaceutical composition comprising a therapeutically effective amount of an IL-17 antibody or antigen binding fragment thereof; b) means for administering the IL-17 antibody or antigen binding fragment thereof to the patient; and c) instructions providing: i) subcutaneously administering the IL-17 antibody or antigen binding fragment thereof to the patient at a dose of about 150 mg during weeks 0, 1, 2, 3, and 4; ii) I) thereafter, subcutaneously administering the IL-17 antibody or antigen binding fragment thereof to the patient at a dose of about 150 mg monthly, beginning during week 8; or II) thereafter, subcutaneously administering the IL-17 antibody or antigen binding fragment thereof to the patient at a dose of about 300 mg during weeks 8, 9 and 12 and then monthly thereafter, beginning during week 16.

Disclosed herein are kits for the treatment of a patient having GPP, comprising: a) a pharmaceutical composition comprising a therapeutically effective amount of an IL-17 antibody or antigen binding fragment thereof; b) means for administering the IL-17 antibody or antigen binding fragment thereof to the patient; and c) instructions providing: i) subcutaneously administering the IL-17 antibody or antigen binding fragment thereof to the patient at a dose of about 150 mg during weeks 0, 1, 2, 3, and 4; ii) assigning the patient to a treatment assessment based on clinical components of a CGI evaluation administered during week 8, wherein assigning a treatment assessment "very much improved" or "much improved" provides an indication that no up-titration is required, and wherein assigning a treatment assessment "worse", "no change" or "minimally improved" provides an indication that up-titration is required; and iii) I) thereafter, subcutaneously administering the IL-17 antibody or antigen binding fragment thereof to the patient at a dose of about 150 mg monthly, beginning during week 8, if no up-titration is required; or II) thereafter, subcutaneously administering the IL-17 antibody or antigen binding fragment thereof to the patient at a dose of about 300 mg during weeks 8, 9 and 12 and then monthly thereafter, beginning during week 16, if up-titration is required.

In some embodiments of the disclosed kits, the patient has von Zumbusch GPP, generalized form of acrodermatitis continua (Hallopeau), acute exanthematic, GPP of pregnancy (impetigo herpetiformis), infantile or juvenile GPP, or circinate or annular GPP.

In some embodiments of the disclosed kits, the clinical components of the CGI are area of erythema with pustules, area of erythema, area of edema and fever.

In some embodiments of the disclosed kits, the patient has a reduction in GPP as assessed by measuring levels of IL-10 and/or IL-22 in response to treatment with the IL-17 antagonist.

In some embodiments of the disclosed kits, the patient has a reduction in disease as assessed by the Japanese Dermatological Association (JDA) severity index for GPP, Clinical Global Impression (CGI) assessment, and/or Psoriasis Area and Severity Index (PAST) in response to treatment with the IL-17 antibody.

In some embodiments of the disclosed kits, the patient has erythema with pustules ≥10% prior to treatment with the IL-17 antibody.

In some embodiments of the disclosed kits, the patient has a Body Surface area Affected (BSA) of at least 5% or greater prior to treatment with the IL-17 antibody.

In some embodiments of the disclosed kits, the patient has a Body Surface area Affected (BSA) of at least 10% or greater prior to treatment with the IL-17 antibody.

In some embodiments of the disclosed kits, the patient is able to stop or reduce concomitant use of a psoriasis agent by at least about 50% in response to treatment with the IL-17 antibody. In some embodiments, the disclosed kits further comprise instructions directing administering the patient at least one additional psoriasis agent. In some embodiments of the disclosed kits, the additional psoriasis agent is selected from the group consisting of ustekinumab, a TNF alpha antagonist (such as etanercept, adalimumab, infliximab), a systemic corticosteroid, cyclosporin, etretinate, and methotrexate.

In some embodiments of the disclosed kits, the patient has GPP without psoriasis vulgaris. In some embodiments of the disclosed kits, the patient has GPP with psoriasis vulgaris. In some embodiments, the patient has a decreased level of Interleukin-36 Receptor Antagonist (e.g., mRNA or protein) in the skin relative to a subject not having GPP. In some embodiments, the patient is selected for treatment with the IL-17 antibody or antigen binding fragment thereof based on having been previously determined to have a decreased level of Interleukin-36 Receptor Antagonist (mRNA or protein) in the skin relative to a subject not having GPP.

Similar kits are envisioned for plaque-type psoriasis and PPP, said kits having appropriate instructions for applying the new dosing regimens plaque-type psoriasis and PPP disclosed herein.

General

In some embodiments, the disclosed methods, treatments, regimens, uses and kits related to GPP, plaque-type psoriasis and PPP employ, instead of an IL-17 antibody, an IL-17 receptor antibody, e.g., an IL-17 receptor antibody having a $K_D$ of about 0.29 nm or about 239 pM (e.g., antibody $AM_H14/AM_L14$ of U.S. Pat. No. 7,767,206, brodalumab, AMG-827, the contents of which are incorporated by reference herein in its entirety).

In some embodiments, the disclosed methods, treatments, regimens, uses and kits related to GPP, plaque-type psoriasis and PPP employ an IL-17 antibody having a $K_D$ of about 1.8 (+/−0.3) pM, binds to an epitope of an IL-17 protein including Ala79, Asp80, Gly81, Asn82, Val83, Asp84, Tyr85, His86, Met87, Asn88, a mean half-life of about 6.5 days following intravenous administration of 1 mg/kg, and/or a mean elimination half-life of about 10.3 days following subcutaneous administration of 1 mg/kg (e.g., antibody mAb126 of U.S. Pat. No. 7,838,638, Ixekizumab, LY2439821, the contents of which are incorporated by reference herein in its entirety).

In some embodiments of the disclosure, the IL-17 antibody or antigen binding fragment thereof is selected from the group consisting of: a) an IL-17 antibody that binds to an epitope of IL-17 comprising Leu74, Tyr85, His86, Met87, Asn88, Val124, Thr125, Pro126, Ile127, Val128, His129; b) an IL-17 antibody that binds to an epitope of IL-17 comprising Tyr43, Tyr44, Arg46, Ala79, Asp80; c) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; d) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-about 200 pM (e.g., as measured by Biacore®), and wherein the IL-17 binding molecule has an in vivo half-life of about 23-about 30 days; and e) an IL-17 antibody that comprises an antibody selected from the group consisting of: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising, in sequence, the hypervariable regions set forth as SEQ ID NO:1, SEQ ID NO:2, and SEQ ID NO:3; v) an immunoglobulin $V_L$ domain comprising, in sequence, the hypervariable regions set forth as SEQ ID NO:4, SEQ ID NO:5 and SEQ ID NO:6; vi) an immunoglobulin $V_H$ domain comprising, in sequence, the hypervariable regions set forth as SEQ ID NO:11, SEQ ID NO:12 and SEQ ID NO:13; vii) an immunoglobulin $V_H$ domain comprising, in sequence, the hypervariable regions set forth as SEQ ID NO:1, SEQ ID NO:2, and SEQ ID NO:3 and an immunoglobulin $V_L$ domain comprising, in sequence, the hypervariable regions set forth as SEQ ID NO:4, SEQ ID NO:5 and SEQ ID NO:6; and viii) an immunoglobulin $V_H$ domain comprising, in sequence, the hypervariable regions set forth as SEQ ID NO:11, SEQ ID NO:12 and SEQ ID NO:13 and an immunoglobulin $V_L$ domain comprising, in sequence, the hypervariable regions set forth as SEQ ID NO:4, SEQ ID NO:5 and SEQ ID NO:6. In some embodiments of the disclosure, the IL-17 antibody or antigen binding fragment thereof is a human antibody. In preferred embodiments of the disclosure, the antibody is secukinumab.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

| | |
|---|---|
| Example 1-Study CAIN457A1302-A multi-center, open label study of subcutaneous secukinumab in prefilled syringes as mono- or co-therapy to assess the efficacy, safety and tolerability up to 52 weeks in Japanese subjects with generalized pustular psoriasis. | |
| Purpose and rationale | The purpose of this study is to assess efficacy and safety data of secukinumab in Japanese subjects with generalized pustular psoriasis (GPP). |
| Primary Objective | To assess the treatment success of secukinumab in subjects with generalized pustular psoriasis (GPP) at Week 16, relative to baseline (BSL). For the primary objective, treatment success is defined as follows: "Minimally improved", "Much improved" or "Very much improved" in Clinical global impression (CGI) |
| Secondary Objectives | To assess the clinically meaningful success of secukinumab in subjects with generalized pustular psoriasis (GPP) at Week 16, relative to baseline (BSL). |

| Example 1-Study CAIN457A1302-A multi-center, open label study of subcutaneous secukinumab in prefilled syringes as mono- or co-therapy to assess the efficacy, safety and tolerability up to 52 weeks in Japanese subjects with generalized pustular psoriasis. | |
|---|---|
| | For the secondary objectives, clinically meaningful success is defined as follows:<br>1) For subjects who receive secukinumab as monotherapy: "Minimally improved", "Much improved" or "Very much improved" in Clinical global impression (CGI)<br>2) For subjects who receive secukinumab as co-medication together with (an) other immunomodulatory drug(s) which is defined as background medication at baseline:<br>a. ONLY IF the co-medication is not meaningfully reduced: "Minimally improved", "Much improved" or "Very much improved" in CGI<br>b. ONLY IF the co-medication is meaningfully reduced: "No change", "Minimally improved", "Much improved" or "Very much improved" in CGI<br>Meaningful reduction of co-medication is defined as follows;<br>Stop of co-medication<br>≥50% reduction of co-medication exposure relative to BSL<br>If subjects are on secukinumab monotherapy, they have to show clinical improvement in order to be considered as subjects with a clinically meaningful success.<br>However, there may be subjects entering the trial because they do not tolerate their previous treatment any more. These subjects may initially receive secukinumab as co-therapy. The original medication would be reduced due to the lack of tolerability. Without secukinumab, this would lead to deterioration of the disease. Hence, for subjects in this category, staying on the same level of response can be considered a clinically meaningful success, IF (and ONLY if) the original medication was meaningfully reduced.<br>To assess the treatment success and the clinically meaningful success of secukinumab in subjects with generalized pustular psoriasis (GPP) at Week 52, relative to BSL (The definitions are the same as described above).<br>To assess the efficacy of secukinumab in subjects with GPP with respect to the CGI over time up to Week 52 relative to BSL.<br>To assess the efficacy of secukinumab in subjects with GPP with respect to the total score and the category of the JDA severity index for GPP over time up to Week 52 relative to BSL.<br>To assess the efficacy of secukinumab in subjects with GPP with respect to the score of the following components of the JDA severity index for GPP over time up to Week 52 relative to BSL:<br>body surface area covered with erythema with pustules<br>body surface area covered with total erythema<br>body surface area covered with edema<br>fever<br>white blood cell count<br>C-reactive protein<br>serum albumin<br>To assess the efficacy of secukinumab in subjects with GPP with respect to the observed value (not scored) of the following components of the JDA severity index for GPP over time up to Week 52 relative to baseline:<br>Percentage of body surface area covered with erythema with pustules<br>Percentage of body surface area covered with total erythema<br>Percentage of body surface area covered with edema<br>fever (body temperature, ° C.)<br>white blood cell count (/μL)<br>C-reactive protein (mg/L)<br>serum albumin (g/dL)<br>To assess the clinical safety and tolerability of secukinumab as assessed by vital signs, clinical laboratory variables, ECGs, and adverse events monitoring over time up to Week 60.<br>To describe the efficacy of secukinumab in subjects with GPP with respect to SF-36 over time up to Week 52 relative to baseline.<br>To describe the efficacy of secukinumab in subjects with GPP with respect to changes in DLQI over time up to Week 52 relative to baseline.<br>To assess the use of systemic co-medication to treat GPP, in subjects who have active GPP treatment at baseline.<br>To describe the use of topical co-medication to treat GPP, in subjects who have active GPP treatment at baseline. |
| Study design | This is a multicenter, single arm, open-label trial in at least 7 (and no more than 15) subjects with GPP. |

Example 1-Study CAIN457A1302-A multi-center, open label study of subcutaneous secukinumab in prefilled syringes as mono- or co-therapy to assess the efficacy, safety and tolerability up to 52 weeks in Japanese subjects with generalized pustular psoriasis.

The study consists of four periods: screening (of up to 4 weeks), induction (of 16 weeks), maintenance (of 36 weeks), and post-treatment follow-up period (of 8 weeks).
Efficacy, safety and PK trough level measurements of secukinumab will be performed according to the visit schedule.
All subjects will receive secukinumab 150 mg (administered subcutaneously) once weekly for four weeks (at BSL, Weeks 1, 2, 3, and 4). Prior to receiving the Week 8 dose, subjects will be assigned to the following treatment group based on the clinical components of their CGI evaluation (area of erythema with pustules, area of erythema, area of edema, and fever) at Week 8:
"No up-titration": In CGI, "Very much improved" or "Much improved": Will continue on secukinumab 150 mg and will receive secukinumab 150 mg every four weeks, starting at Week 8, until and including Week 48.
"Up-titration": In CGI, "Worse, "No change" or "Minimally improved", in which up-titration is considered appropriate by the investigator: Will receive secukinumab 300 mg on Weeks 8, 9, and 12, and then every four weeks until and including Week 48.
Subjects receiving secukinumab 150 mg and assessed as "Worse change", or "Minimally improved" in CGI can be up-titrated to secukinumab 300 mg at any visit starting at Week 16, if considered appropriate by the investigator. These subjects will receive secukinumab 300 mg at each regular scheduled visit up to Week 48. Once subjects receive secukinumab at the dose of 300 mg, there is no reduction back to the dose of 150 mg.
Screening period (Screening to BSL)
The screening period of up to 4 weeks will be used to assess eligibility of the subjects and to taper subjects off disallowed medications.
Induction period (BSL to Week 16 pre-dose)
The induction period is BSL through Week 16 (prior to Week 16 dose). At the start of the induction period, eligible subjects will be entered into the open label treatment group (secukinumab 150 mg, administered subcutaneously).
During the induction period, subjects will be visiting the study site at BSL and Weeks 1, 2, 3, and 4, and will receive secukinumab 150 mg once weekly for four weeks (BSL and Weeks 1, 2, 3, and 4). Prior to receiving the Week 8 dose, all subjects in the secukinumab 150 mg group will be assigned to one of two treatment groups ("up-titration" or "no up-titration") as explained above, and will receive the appropriate secukinumab dose.
Assessments for the primary endpoint will be done at Week 16 prior to the dose at Week 16. In addition, for subjects who discontinue study treatment prematurely for any reason before the end of the induction period, Week 16 (planned End of Induction Period (EOI) must be performed approximately four weeks after their last dose of study treatment (secukinumab) and then the subject should enter the follow-up period.
Subjects receiving secukinumab 150 mg and assessed as "Worse change", "Minimally improved" in CGI can be up-titrated to secukinumab 300 mg at any visit starting at Week 16, if considered appropriate by the investigator. These subjects will receive secukinumab 300 mg at each regular scheduled visit up to Week 48. Once subjects receive secukinumab at the dose of 300 mg, there is no reduction back to the dose of 150 mg.
Maintenance period (Week 16 post-dose to Week 52)
The maintenance period is defined as Week 16 post-dose through Week 52. During the maintenance period, subjects will be visiting the study site every four weeks, starting at Week 16, up to Week 52, and will receive s.c. study treatment every four weeks starting at Week 16, and up to Week 48. During the maintenance period, up-titration to 300 mg is permitted at any visit. Down-titration from 300 mg to 150 mg is not permitted. If the investigator considers up-titration, the investigator should follow the instructions as describe above (see induction period).
Subjects who finish the maintenance treatment period will either enter the treatment-free follow-up period, or may be offered participation in an extension study (if available).
In addition, for subjects who discontinue study treatment prematurely for any reason before the end of the maintenance period, Week 52 (planned End of Maintenance Period (EOM) visit) must be performed approximately four weeks after their last dose of secukinumab, and then the subject should enter the follow-up period.
Post-treatment follow-up period (Week 52 to Week 60)
Post-treatment follow-up visits (no study treatment administered during follow-up period) will be at Week 56 (Follow-up visit F4, which is 4 weeks post maintenance period, but 8 weeks post last dose of secukinumab), -continued Example 1-Study CAIN457A1302-A multi-center, open label study of subcutaneous
secukinumab in prefilled syringes as mono- or co-therapy to assess the efficacy, safety
and tolerability up to 52 weeks in Japanese subjects with generalized pustular psoriasis.

| | |
|---|---|
| | and at Week 60 (Follow-up visit F8 (or End of Post-treatment Follow-up (EOF)), which is 8 weeks post maintenance period, but 12 weeks post last dose of secukinumab. |
| Population | The study population will consist of male or female outpatients or inpatients (≥18 years old) with generalized pustular psoriasis (GPP). Inpatients are defined as subjects who have been admitted to the hospital due to GPP, but not enrolled in this study before admission. These subjects may participate in the study. |
| Inclusion criteria | Subjects eligible for inclusion in this study must fulfill all of the following criteria:<br>1. Subjects must be able to understand and communicate with the investigator and comply with the requirements of the study and must give a written, signed and dated informed consent before any study related activity is performed. Where relevant, a legal representative will also sign the informed study consent according to local laws and regulations.<br>2. Men or women at least 18 years of age at time of screening.<br>3. At BSL: Presence of GPP classified on the basis of the criteria for diagnosis of GPP by Japanese Dermatological Association. Systemic symptoms such as fever and fatigue (subjects in whom occurrence of systemic symptoms in the past is confirmed can also be enrolled). Sterile pustules on erythema spread over the whole body or in wide areas of the body, which can sometimes coalesce into larger lakes of pustules. Histopathologically, forming neutrophilic subcorneal pustule characterized by spongiform pustule of Kogoj.<br>4. At BSL: Erythema area with pustule ≥ 10% |
| Investigational and reference therapy | Investigational Drug:<br>Secukinumab 150 mg, provided in a 1 mL prefilled syringe (one syringe for 150 mg dose, two syringes for the 300 mg dose) |
| Efficacy assessments | Japanese Dermatological Association (JDA) severity index for GPP (JDA severity Index for GPP; total score 0-17. Assessment of skin lesions: area of erythema with pustules, area of erythema, and area of edema; each score 0-3. Assessment of systemic manifestations and laboratory findings: fever, WBC count, CRP and serum albumin; each score 0-2.)<br>Clinical Global Impression (CGI)<br>Psoriasis Area and Severity Index (PASI; score 0-72) |
| Safety assessments | Evaluation of all AEs and SAEs including injection site hypersensitivity reactions, vital signs, laboratory assessments and occurrence of infections.<br>Physical examination<br>Vital signs<br>Height and weight<br>Laboratory evaluations<br>Hematology<br>Clinical chemistry<br>Urinalysis<br>Immunogenicity (assessment of anti-secukinumab antibody development)<br>Electrocardiogram (ECG)<br>Pregnancy and assessments of fertility |
| Other assessments | Health-Related Quality of Life (HRQoL) assessments:<br>DLQI<br>SF-36v2<br>Pharmacokinetics<br>Photography (optional) |
| Data analysis | The primary efficacy variable is the proportion of subjects who experience treatment success at Week 16 relative to baseline (BSL). The analysis of the primary variable will be based on the FAS. |

The clinical trial design for CAIN457A1302 is shown in FIG. 1. Early results from study CAIN457A1302 are shown in FIG. 2. In FIG. 2A it can be seen that the key symptom of GPP (erythema with pustules) can be significantly reduced by treatment with secukinumab in the majority of patients. In some patients, complete clearance of this symptom is observed within 3 weeks after starting treatment. At the same time, a key symptom of plaque psoriasis, erythema, is also reduced in the majority of patients (FIG. 2B), but this occurs more slowly and less frequently with complete clearance. This shows that erythema as an isolated symptom, such as may occur with plaque-type psoriasis, reacts differently from the more typical GPP symptom of erythema with pustules, underscoring the difference between the two diseases and the difference in treatment response. In general, GPP patients' response to secukinumab (1-3 weeks) was faster than plaque-type psoriasis patients' response to secukinumab (usually 3-4 weeks). Moreover, GPP patients generally did not need up-titration to 300 mg secukinumab, as 150 mg secukinumab was sufficient to achieve symptom clearance. Both the rapidity and the strength of secukinumab in treating GPP was surprising compared to plaque-type psoriasis, as GPP is generally considered a more severe disease that plaque-type psoriasis.

Example 2—Study CAIN457A1302-Dose and Dosing Regimen Rationale

Different options for up-titration regimens were explored in model-based simulations, regarding their expected impact on concentration levels and clinical response.

The relationship between secukinumab dose/regimen, secukinumab concentration and the PASI response has previously been modeled using a population-PK/PD approach. The model has been built and updated incrementally with data from patients with moderate-to-severe chronic plaque-type psoriasis from the phase 2 studies CAIN457A2102, CAIN457A2103, CAIN457A2211, CAIN457A2212, and CAIN457A2220.

Concentration profiles of secukinumab are described by a two-compartment model, with combined first-order absorption to reflect subcutaneous administration and zero-order absorption to reflect intravenous administration. PASI score profiles are characterized by a turnover (indirect response) model. The drug effect acts on the turnover model via an Emax-function, driven by secukinumab concentration in the central compartment. Inter-individual variability is estimated as a random effect on PK parameters (clearance, volume of distribution, inter-compartmental clearance, volume of distribution of peripheral compartment, bioavailability, and absorption rate), and PD parameters (turnover out-rate kout, PASI steady state level, and $EC_{50}$). Model qualification was performed using standard assessment methods (goodness-of-fit analysis, predictive checks, and external validation based on prospective predictions).

Based on this model and the final parameter estimates, outcomes for new dosing regimens were simulated. The simulations were performed in order to design an "up-titration" dosing regimen to address the following question: How can a patient that started with treatment on the 150 mg regimen and that is in need for treatment intensification be up-titrated to 300 mg such that the same exposure level as in a patient starting on a 300 mg regimen is approached rapidly?

The simulation is based on the assumption that the PK and PK/PD relationships modeled in chronic plaque-type psoriasis are reasonable approximations of the PK and PK/PD relationships in patients with generalized pustular psoriasis. To adjust for a Japanese patient population, a "typical" bodyweight of 70.8 kg (instead of 90 kg as for a general psoriasis population) was used.

Figure 3:
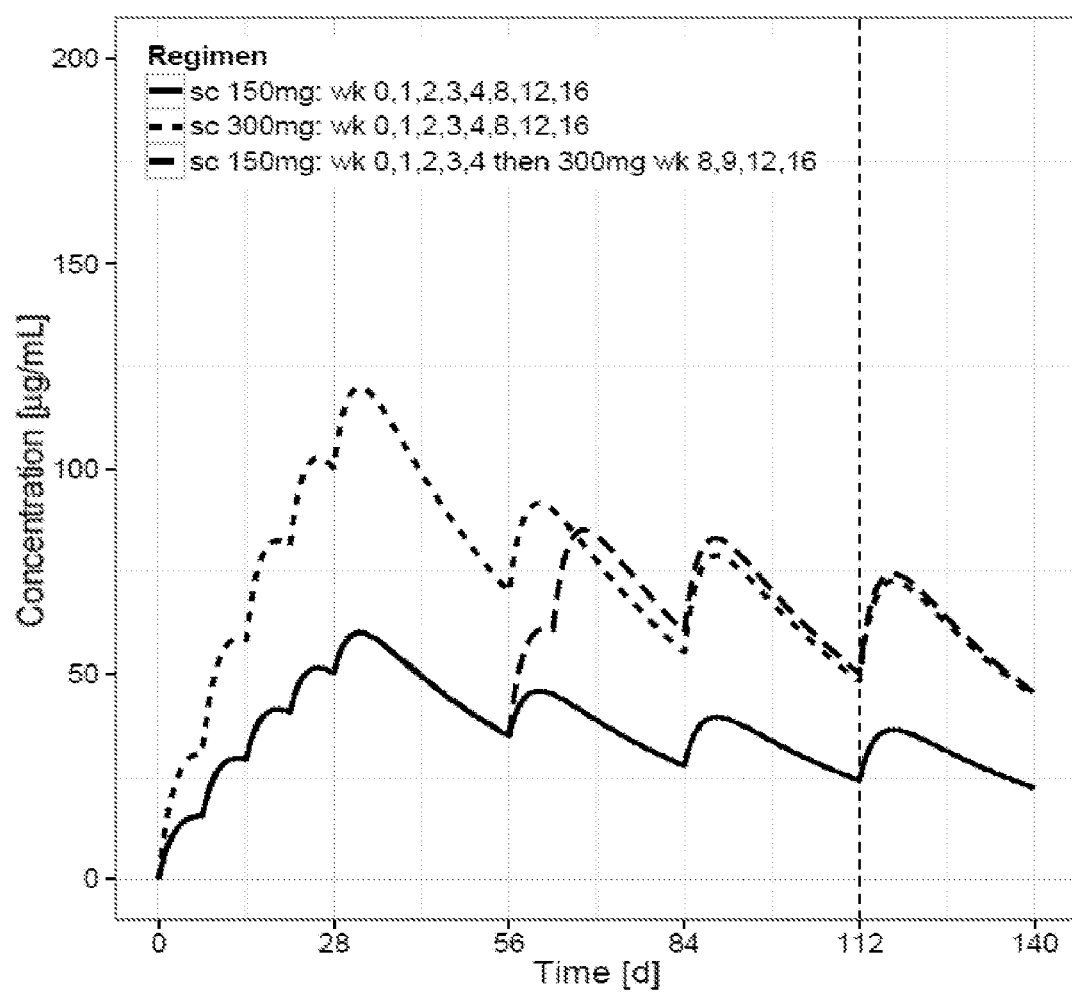
FIG. 3: Provides simulated concentration profiles in plaque-type psoriasis. Shown are the simulated concentration profiles for the two dose-regimens (150 mg and 300 mg) used in large phase 3 for plaque psoriasis, plus for the "up-titration" GPP dose-regimen (secukinumab 150 mg at baseline [BSL—Week 0], Weeks 1, 2, 3, and 4 and secukinumab 300 mg during Weeks 8, 9, 12 and 16).

As shown in FIG. 3, after a starting regimen of 150 mg s.c. at weeks 0, 1, 2, 3, 4, the proposed up-titration regimen of 300 mg given at weeks 8, 9, and 12 rapidly approaches the same exposure levels as the regimen that starts with 300 mg doses.

Figure 4:
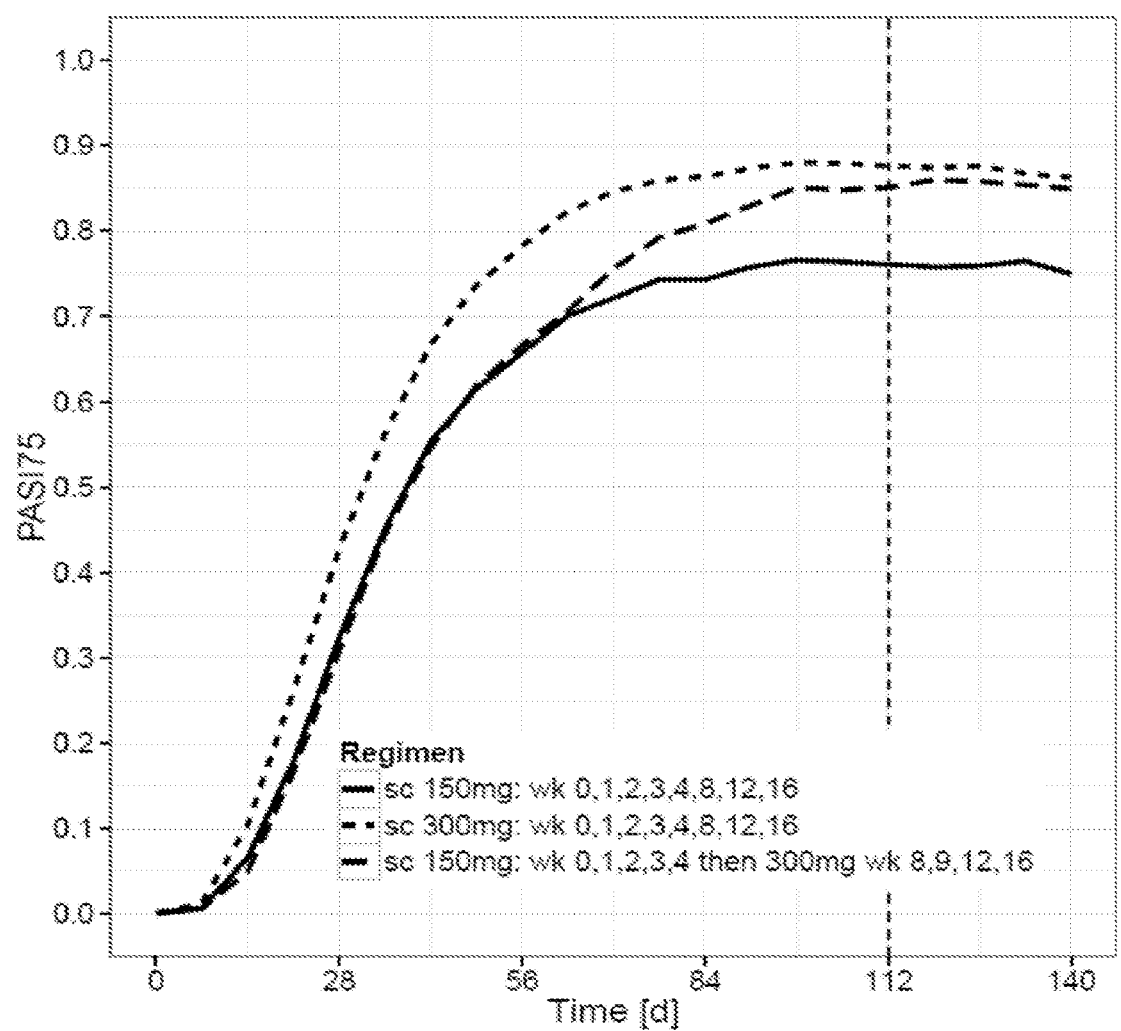
FIG. 4: Provides simulated PASI 75 response rate in plaque psoriasis. Shown are the simulated PASI 75 response rates for the two dose-regimens (150 mg and 300 mg) used in large phase 3 for plaque psoriasis, plus for the "up-titration" GPP dose-regimen (secukinumab 150 mg at baseline [BSL—Week 0], Weeks 1, 2, 3, and 4 and secukinumab 300 mg during Weeks 8, 9, 12 and 16).

FIG. 4 gives the model-based simulation of PASI75 responder rate for the 150 mg regimen, the 300 mg regimen, and the up-titration regimen in moderate-to-severe chronic plaque-type psoriasis. After up-titration the expected response is approaching the response levels expected for the 300 mg regimen. While the 300 mg PK levels are reached approximately 2 weeks after up-titration, the catching-up of clinical response is expected to reach similar levels after 2-3 months.

This suggests that up-titration to secukinumab 300 mg, and adding one additional dose at Week 9, might result in a better response for those subjects initially not responding well enough.

In this study, subjects will continue treatment with secukinumab for 52 Weeks. This will provide information about long-term efficacy and safety data pertaining to the subjects with GPP treated with secukinumab.

Example 3—Dosage and Dosing Rationale for Improved Treatment Regimen for Plaque-Type Psoriasis—Up-Titration To explore options for improved treatment regimens in plaque-type psoriasis, pharmacokinetic profiles were simulated for up-titration at Week 12. The simulation is based on the same model as in Example 3 (fitted with data from patients with moderate-to-severe chronic plaque-type psoriasis from the phase 2 studies CAIN457A2102, CAIN457A2103, CAIN457A2211, CAIN457A2212, and CAIN457A2220). For the simulation, a plaque-type psoriasis population was simulated with an average bodyweight of about 90 kg and accounting for between-patient differences in pharmacokinetic parameters (random effect parameters in the population-pharmacokinetic model).

Figure 5:
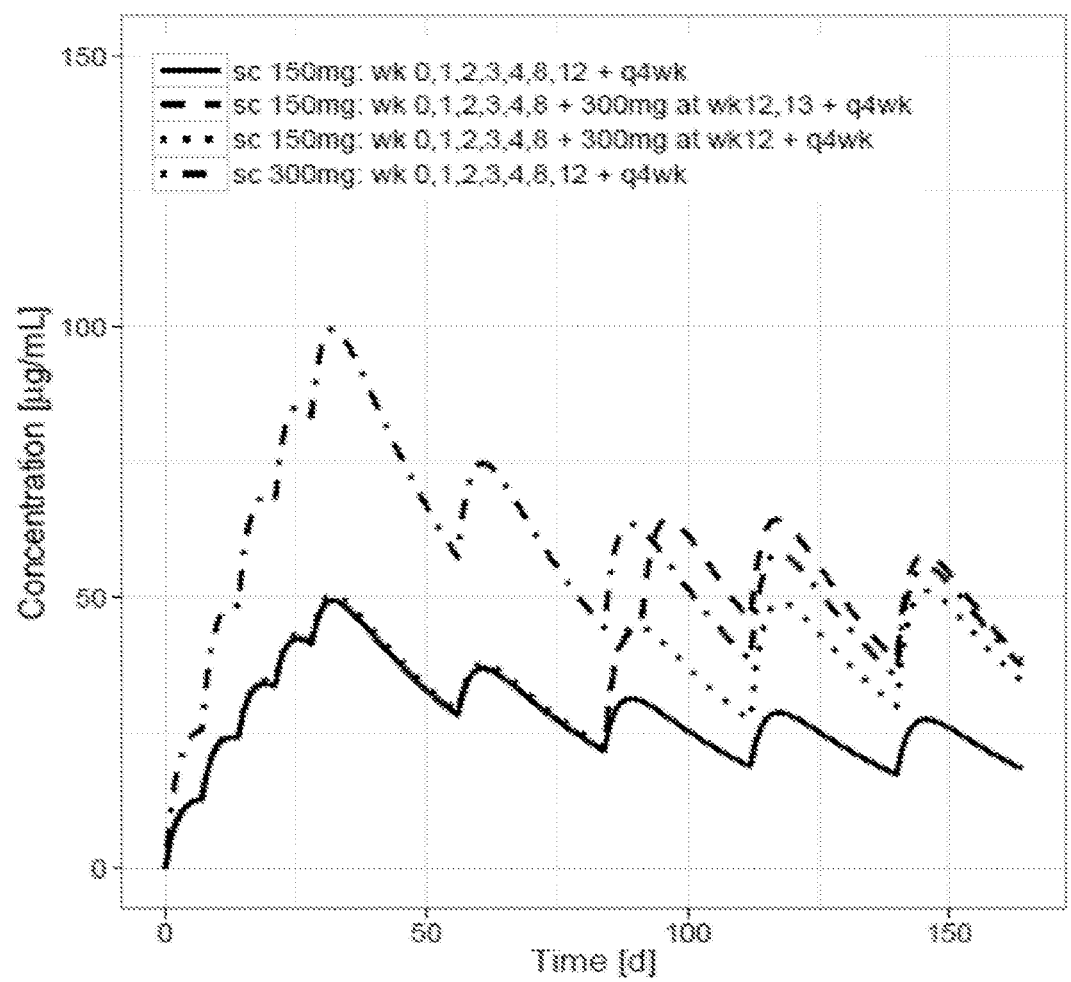
FIG. 5: Provides simulated concentration profiles in plaque psoriasis. Shown are the simulated concentration profiles for the two dose-regimens (150 mg and 300 mg) used in phase 3 for plaque psoriasis, plus for two "up-titration" plaque-type psoriasis dose-regimens (secukinumab 150 mg at baseline [BSL—week 0], weeks 1, 2, 3, 4, 8 and secukinumab 300 mg during week 12 (or week 12 and 13) and week 16).

FIG. 5 shows the two regimens studied in phase 3 of either 150 mg or 300 mg s.c. given at weeks 0, 1, 2, 3, 4, and 8+q4wk as solid and dash-dot line, respectively. For the two explored alternative up-titration regimens, it can be seen that after a starting regimen of 150 mg s.c. at weeks 0, 1, 2, 3, 4, and 8 an up-titration to 300 mg given at Weeks 12, 13, 16+q4wk (dashed line) approaches the exposure levels of the regimen starting at 300 mg more rapidly than up-titrating at weeks 12, 16+q4wk without the dose at week 13 (dotted line).

Figure 6:
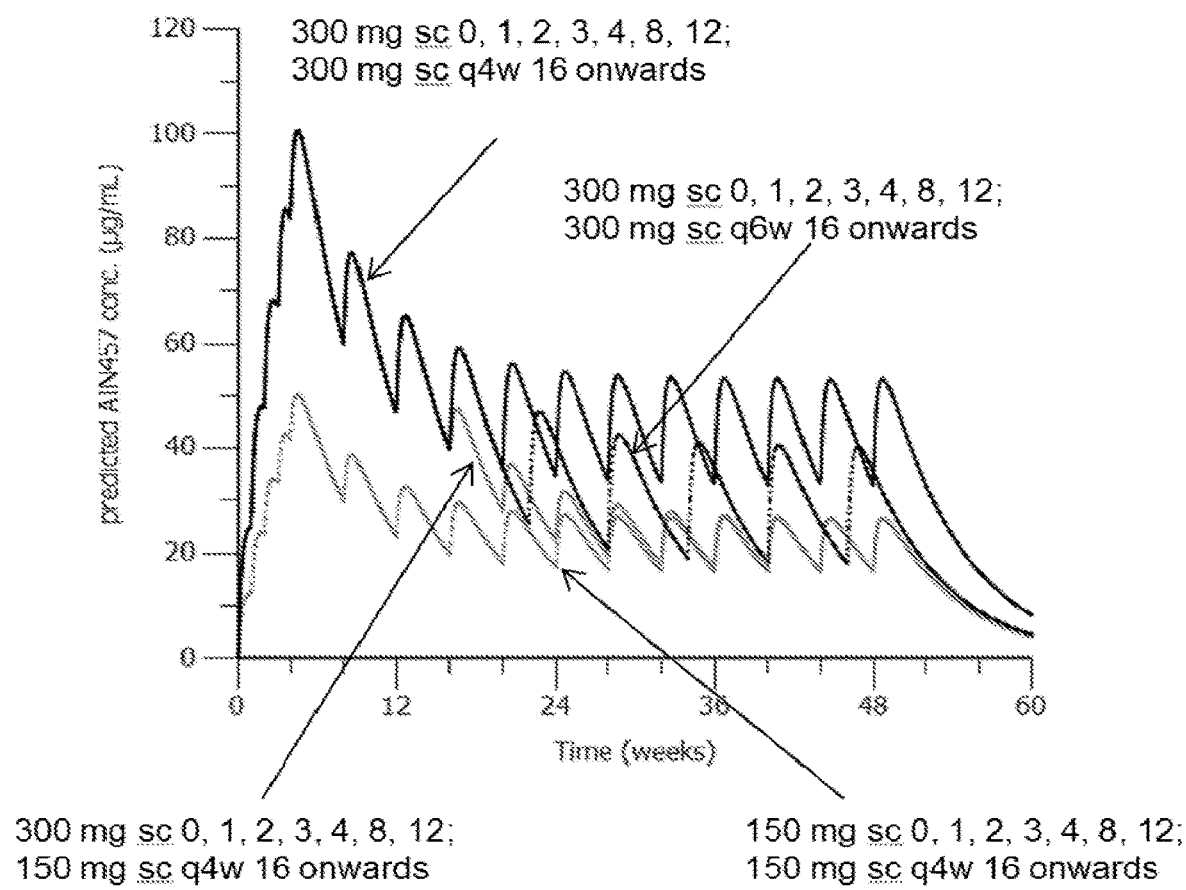
FIG. 6: Provides simulated time-concentration profiles in plaque psoriasis. Shown are the simulated concentration profiles of secukinumab (AIN457) for the two dose-regimens (150 mg and 300 mg) used in large phase 3 for plaque psoriasis, plus one "down-titration" plaque-type psoriasis dose-regimen (secukinumab 300 mg at baseline [BSL—week 0], weeks 1, 2, 3, 4, 8, 12 and secukinumab 150 mg q4 weeks from week 16) plus one regimen with maintenance dosing at every six weeks (secukinumab 300 mg at baseline [BSL—week 0], weeks 1, 2, 3, 4, 8, 12 and secukinumab 300 mg q6 weeks from week 16).

Example 4—Dosage and Dosing Rationale for Improved Treatment Regimen for Plaque-Type Psoriasis—q6w Maintenance Regimen To explore options for improved treatment regimens in plaque-type psoriasis, pharmacokinetic and PASI90 response profiles were simulated for down-titration at Week 12 and decreased frequency of dosing beginning at Week 16. For the pharmacokinetic simulation, a plaque-type psoriasis population was simulated with an average bodyweight of about 90 kg FIG. 6 shows simulated secukinumab (AIN457) concentration for the two regimens studied in large phase 3 clinical trials of either 150 mg or 300 mg s.c. given at weeks 0, 1, 2, 3, 4, and 8+q4wk as gray-dotted and black-solid line, respectively. For the explored alternative regimens, it can be seen that after a starting regimen of 300 mg s.c. at weeks 0, 1, 2, 3, 4, 8 and 12, a 300 mg q6w maintenance regimen (black-dotted line) will be between the 150 and 300 mg q4w maintenance exposure levels. Further, down-titration to 150 mg q4w from Week 16 onwards after starting with 300 mg sc at Weeks 0, 1, 2, 3, 4, 8 and 12 would lead to a comparable exposure as for the constant 150 mg phase 3 regimen already at Week 28 (gray-solid line).

Figure 7:
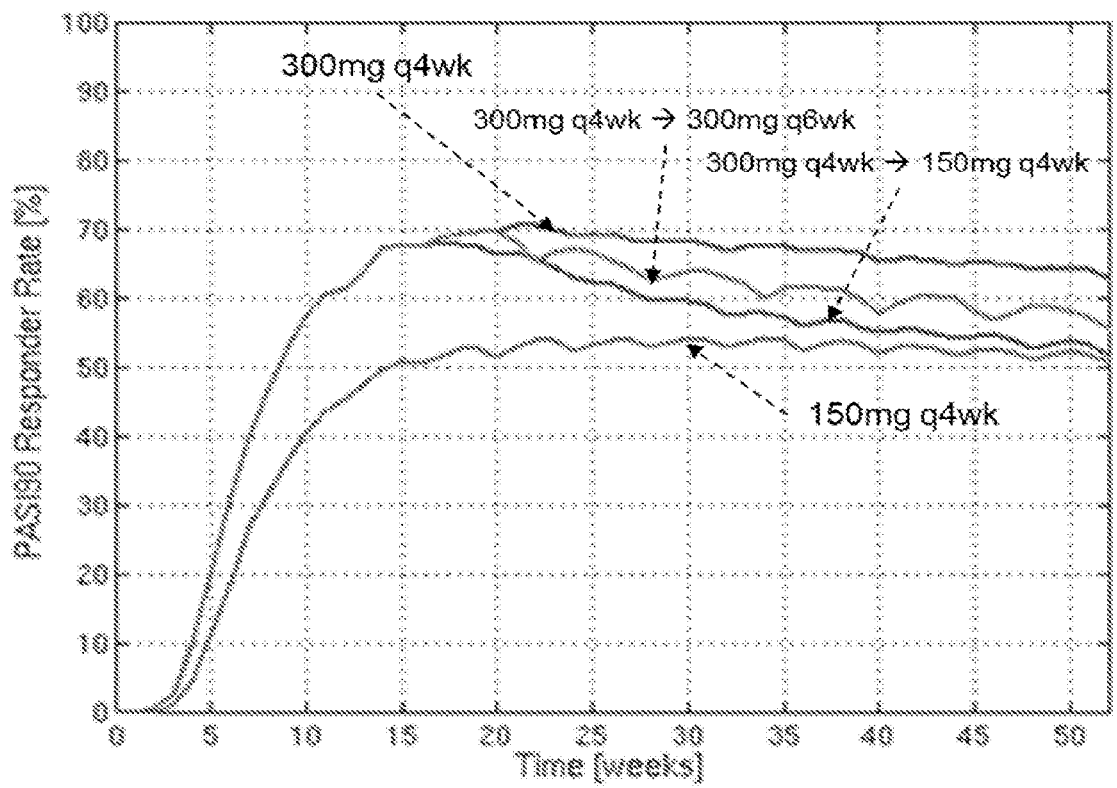
FIG. 7: Provides simulated PASI90 response rate in plaque psoriasis. Shown are the simulated PASI90 profiles for the two dose-regimens (150 mg and 300 mg) used in large phase 3 for plaque psoriasis, plus one "down-titration" plaque-type psoriasis dose-regimen (secukinumab 300 mg at baseline [BSL—week 0], weeks 1, 2, 3, 4, 8, 12 and secukinumab 150 mg q4 weeks from week 16) plus one regimen with maintenance dosing at every six weeks (secukinumab 300 mg at baseline [BSL—week 0], weeks 1, 2, 3, 4, 8, 12 and secukinumab 300 mg q6 weeks from week 16).

FIG. 7 shows the simulated PASI90 responder rates for two regimens studied in large phase 3 clinical trials of either 150 mg or 300 mg s.c. given at weeks 0, 1, 2, 3, 4, and 8+q4wk. For the explored alternative regimen, it can be seen that after a starting regimen of 300 mg s.c. at weeks 0, 1, 2, 3, 4, 8 and 12, a 300 mg q6w maintenance regimen, as well as a down titration to 150 mg q4w from Week 16, will lead to PASI90 response profiles that are below the responder rates for 300 mg q4w (and above those for 150 mg q4wk).

Example 5—Pharmokinetic (PK) Information for Seckukinumab

Based on data obtained from various plaque-type psoriasis studies, the following PK information is provided for seckukinumab (Table 6).

TABLE 6

Pharmokinetic values for secukinumab. Experimental PK values are compiled from various secukinumab psoriasis trials. Simulated values are provided for the indicated psoriasis dosing regimens.

| | |
|---|---|
| Experimental | Induction<br>mean trough level one month after a 4$^{th}$ dose of 150 mg delivered s.c. at weeks 0, 1, 2 and 4 ~29.2 µg/mL, with a 30-40% inter-patient variation<br>Maintenance<br>average steady-state trough levels ~15 µg/ml (for a monthly [every 4 weeks] 150 mg regimen), with a 30-40% inter-patient variation |
| Simulated | Induction (150 or 300 mg delivered s.c. weeks 0, 1, 2, 3, 4, and 8)<br>$C_{max}$ (around 32 days) for a typical 90 kg patient:<br>~52 µg/ml (for 150 mg regimen)<br>~104 µg/ml (for 300 mg regimen)<br>Maintenance (150 or 300 mg delivered s.c. monthly [every 4 weeks] beginning week 12) |

TABLE 6-continued

Pharmokinetic values for secukinumab. Experimental PK values are compiled from various secukinumab psoriasis trials. Simulated values are provided for the indicated psoriasis dosing regimens.

Average steady-state trough levels for a typical 90 kg psoriasis patient:
~16 µg/ml (for a monthly [every 4 weeks] 150 mg regimen)
~33 µg/ml (for a monthly [every 4 weeks] 300 mg regimen)
95% of the population are predicted to be in the range:
5-33 µg/ml (for a monthly [every 4 weeks] 150 mg regimen)
11-70 µg/ml (for a monthly [every 4 weeks] 300 mg regimen)

In addition, it has been determined that secukinumab has a $T_{max}$ of about 7-8 days, and an elimination half-life of about 30 days. The PK information provided in this Example can be used to design different dosing regimens for treatment of GPP, e.g., delivery of a different dosage of the IL-17 binding molecule (e.g., an IL-17 antibody, e.g., secukinumab) from the dosage used in the Examples or delivery of the same dosage as used in the Examples, but which is provided at a different time point from the time points used in the Examples. By maintaining the same PK profile, even though a dosing regimen may change, a skilled artisan is able to use an IL-17 antibody other than secukinumab for the treatment of GPP.

What is claimed is:

1. A method of treating palmoplantar pustular psoriasis (PPP), comprising administering secukinumab to a patient in need thereof, wherein secukinumab is administered to the patient by subcutaneous injection at a dose of about 150 mg-about 300 mg at weeks 0, 1, 2, 3, and 4, and then every four weeks thereafter.

2. The method according to claim 1, wherein all doses are about 150 mg or about 300 mg.

3. The method according to claim 1, wherein each dose is about 150 mg.

4. The method according to claim 3, wherein each dose is administered in a volume of 1 milliliter.

5. The method according to claim 1, wherein each dose is about 150 mg, wherein secukinumab is formulated in a pharmaceutical composition comprising a buffer and a stabilizer, wherein the pharmaceutical composition is disposed in an autoinjector, and wherein the pharmaceutical composition delivery volume is 1 milliliter.

6. The method according to claim 1, wherein each dose is about 150 mg, and wherein secukinumab is disposed in a pre-filled syringe, a vial, an injection pen, or an autoinjector.

7. The method according to claim 1, wherein each dose is about 300 mg.

8. The method according to claim 7, wherein each dose is administered in a volume of 2 milliliters.

9. The method according to claim 1, wherein each dose is about 300 mg, wherein secukinumab is formulated in a pharmaceutical composition comprising a buffer and a stabilizer, wherein the pharmaceutical composition is disposed in an autoinjector, and wherein the pharmaceutical composition delivery volume is 2 milliliters.

10. The method according to claim 1, wherein each dose is about 300 mg, and wherein secukinumab is disposed in a pre-filled syringe, a vial, an injection pen, or an autoinjector.

11. The method according to claim 1, wherein secukinumab is formulated in a pharmaceutical composition comprising a buffer and a stabilizer.

12. The method according to claim 1, further comprising administering to the patient at least one additional psoriasis agent.

13. The method according to claim 12, wherein the at least one additional psoriasis agent is selected from the group consisting of ustekinumab, a TNF alpha antagonist, a systemic corticosteroid, cyclosporin, etretinate, and methotrexate.

14. The method according to claim 1, wherein the method further comprises administering to the patient an additional psoriasis agent in an amount at least 50% less than the amount when the psoriasis agent is used without the secukinumab treatment.

15. The method according to claim 1, wherein the patient has PPP without psoriasis vulgaris.

16. The method according to claim 1, wherein the patient has PPP with psoriasis vulgaris.

* * * * *